United States Patent
Wu et al.

(10) Patent No.: US 12,409,449 B2
(45) Date of Patent: Sep. 9, 2025

(54) FLOW CELLS

(71) Applicant: ILLUMINA, INC., San Diego, CA (US)

(72) Inventors: Yir-Shyuan Wu, Albany, CA (US); Tarun Kumar Khurana, Fremont, CA (US); Yasaman Farshchi, San Francisco, CA (US); Xi-Jun Chen, San Carlos, CA (US); Bernard Hirschbein, San Francisco, CA (US)

(73) Assignee: Illumina, Inc., San Diego, CA (US)

( * ) Notice: Subject to any disclaimer, the term of this patent is extended or adjusted under 35 U.S.C. 154(b) by 1041 days.

(21) Appl. No.: 17/420,048

(22) PCT Filed: Jul. 22, 2020

(86) PCT No.: PCT/US2020/043057
§ 371 (c)(1),
(2) Date: Jun. 30, 2021

(87) PCT Pub. No.: WO2021/021515
PCT Pub. Date: Feb. 4, 2021

(65) Prior Publication Data
US 2022/0080415 A1    Mar. 17, 2022

Related U.S. Application Data

(60) Provisional application No. 62/881,597, filed on Aug. 1, 2019.

(51) Int. Cl.
*B01L 3/00* (2006.01)
*C08F 220/56* (2006.01)
(Continued)

(52) U.S. Cl.
CPC ... *B01L 3/502715* (2013.01); *B01L 3/502707* (2013.01); *C08F 220/56* (2013.01);
(Continued)

(58) Field of Classification Search
CPC ......... B01L 3/502715; B01L 3/502707; B01L 2200/0689; B01L 2200/16;
(Continued)

(56) References Cited

U.S. PATENT DOCUMENTS

| | | |
|---|---|---|
| 8,117,902 B2 | 2/2012 | Santore et al. |
| 2004/0086870 A1 | 5/2004 | Tyvoll et al. |

(Continued)

FOREIGN PATENT DOCUMENTS

| | | |
|---|---|---|
| CN | 103443624 A | 12/2013 |
| KR | 1020140045780 A | 4/2014 |

(Continued)

OTHER PUBLICATIONS

Unknown Author, "Polylysine surfaces", Web page <https://www.proteinslides.com/polylysine>, 2 pages, retrieved Jun. 27, 2019.
(Continued)

*Primary Examiner* — Jill A Warden
*Assistant Examiner* — Alex Ramirez
(74) *Attorney, Agent, or Firm* — Dierker & Kavanaugh, P.C.

(57) ABSTRACT

An example of a flow cell includes a substrate and a cationic polymeric hydrogel on the substrate. The cationic polymeric hydrogel includes a cationic moiety that is i) integrated into a monomeric unit of an initial polymeric hydrogel or ii) attached to the monomeric unit of the initial polymeric hydrogel through a linker. The flow cell further includes an amplification primer attached to the cationic polymeric hydrogel.

21 Claims, 10 Drawing Sheets

(51) Int. Cl.
  *C08J 9/36* (2006.01)
  *C12Q 1/6806* (2018.01)

(52) U.S. Cl.
  CPC ............ *C08J 9/365* (2013.01); *C12Q 1/6806* (2013.01); *B01L 2200/0689* (2013.01); *B01L 2200/16* (2013.01); *B01L 2300/069* (2013.01); *B01L 2300/0877* (2013.01); *C08J 2205/022* (2013.01); *C08J 2333/26* (2013.01)

(58) Field of Classification Search
  CPC ......... B01L 2300/069; B01L 2300/087; B01L 2300/07; C08F 220/56; C12Q 1/6806; C08J 2205/022; C08J 2333/26
  See application file for complete search history.

(56) References Cited

U.S. PATENT DOCUMENTS

| | | |
|---|---|---|
| 2013/0157278 A1 | 6/2013 | Atrazhev |
| 2018/0045713 A1 | 2/2018 | Janssen et al. |
| 2018/0327832 A1* | 11/2018 | Ramirez ............ B01L 3/502707 |
| 2020/0216895 A1* | 7/2020 | Khurana ............... C12Q 1/6874 |
| 2020/0230598 A1 | 7/2020 | Drews et al. |

FOREIGN PATENT DOCUMENTS

| | | |
|---|---|---|
| KR | 1020150006223 A | 1/2015 |
| RU | 2713089 C1 | 2/2020 |
| TW | 200424519 A | 11/2004 |
| TW | I271218 B | 1/2007 |
| TW | 201441607 A | 11/2014 |
| WO | 2000056444 A2 | 9/2000 |
| WO | 2004086046 A1 | 10/2004 |
| WO | 2008030395 A1 | 3/2008 |
| WO | 2013188582 A1 | 12/2013 |
| WO | 2014059446 A1 | 4/2014 |
| WO | 2019126040 A1 | 6/2019 |

OTHER PUBLICATIONS

Gryadunov et al., "The EIMB Hydrogel Microarray Technology: Thirty Years Later", Acta Naturae, vol. 10, No. 4 (39), Sep. 24, 2018, p. 4-18, 2018.

* cited by examiner

*Fig-9A*  200 um 200 um 100 um

FLOW CELLS

CROSS-REFERENCE TO RELATED APPLICATION

This application claims the benefit of U.S. Provisional Application Ser. No. 62/881,597, filed Aug. 1, 2019; the content of which is incorporated by reference herein in its entirety.

BACKGROUND

There are a variety of methods and applications for which it is desirable to generate a library of fragmented and tagged deoxyribonucleic acid (DNA) molecules from double-stranded DNA (dsDNA) target molecules. Often, the purpose is to generate smaller DNA molecules (e.g., DNA fragments) from larger dsDNA molecules for use as templates in DNA sequencing reactions. The templates may enable short read lengths to be obtained. During data analysis, overlapping short sequence reads can be aligned to reconstruct the longer nucleic acid sequences. In some instances, pre-sequencing steps (such as barcoding of particular nucleic acid molecules) can be used to simplify the data analysis.

INTRODUCTION

A first aspect disclosed herein is a flow cell comprising a substrate; a cationic polymeric hydrogel on the substrate, the cationic polymeric hydrogel including a cationic moiety i) integrated into a monomeric unit of an initial polymeric hydrogel or ii) attached to the monomeric unit of the initial polymeric hydrogel through a linker; and an amplification primer attached to the cationic polymeric hydrogel.

In an example of the first aspect, the monomeric unit is N-(5-bromoacetamidylpentyl)acrylamide; the cationic moiety is a phosphonium cation; and the phosphonium cation displaces a bromine of the N-(5 bromoacetamidylpentyl) acrylamide. In an example, the phosphonium cation is selected from the group consisting of a tris(hydroxymethyl) phosphonium cation, a tris(hydroxypropyl)phosphonium cation, a tetrakis(hydroxymethyl)phosphonium cation, and a tris(2-carboxyethyl)phosphonium cation.

In another example of the first aspect, i) the monomeric unit includes a terminal azide group and the linker includes an alkyne group; or ii) the monomeric unit includes a terminal alkyne group and the linker includes an azide group. In an example, the cationic moiety includes a protonated amine group, a sulfonium ion, a quaternary ammonium cation, or combinations thereof. In another example, the monomeric unit is N-(5-azidoacetamidylpentyl)acrylamide; and the cationic moiety is an N,N,N-trimethylethanolammonium cation. In still another example, the linker further includes a cleavable disulfide bond, a photocleavable bond, a cleavable phosphodiester bond, or combinations thereof.

In yet another example of the first aspect, the monomeric unit is N-(5-azidoacetamidylpentyl)acrylamide; the linker includes a terminal alkyne group and a terminal bromine; and the cationic moiety is a phosphonium cation that displaces the terminal bromine.

In an example of the first aspect, the substrate includes a plurality of depressions separated by interstitial regions, and wherein the cationic polymeric hydrogel is positioned within each of the depressions. In an example, the substrate further comprises a plurality of chambers, and wherein a sub-set of the plurality of depressions are located within a perimeter of each of the plurality of chambers.

It is to be understood that any features of the flow cell disclosed herein may be combined together in any desirable manner and/or configuration to achieve the benefits as described in this disclosure, including, for example, positive charges to attract and spatially confine library fragments.

A second aspect disclosed herein is a method comprising introducing a fluid, including a positively chargeable moiety, to a flow cell including an initial polymeric hydrogel having a surface moiety selected from the group consisting of a negatively chargeable atom, an azide group, and an alkyne group; and an amplification primer attached to the initial polymeric hydrogel; and incubating the initial polymeric hydrogel in the fluid at a temperature and for a time, thereby forming a cationic polymeric hydrogel including a cationic moiety.

In an example of the second aspect, the positively chargeable moiety displaces the negatively chargeable atom of the initial polymeric hydrogel. In an example, the surface moiety is the negatively chargeable atom; the negatively chargeable atom is bromine; and the positively chargeable moiety is selected from the group consisting of tris(hydroxymethyl) phosphine, tris(hydroxypropyl)phosphine, tetrakis(hydroxymethyl)phosphine, and tris(2-carboxyethyl)phosphine. In an example, the fluid further includes a buffer having a pH ranging from 6 to 12. In an example, the temperature ranges from about 18° C. to about 65° C. and the time ranges from about 1.5 minutes to about 5 minutes.

In another example of the second aspect, the surface moiety is the azide group or the alkyne group; and the positively chargeable moiety covalently attaches to the surface moiety through a linker. In an example, the surface moiety is the azide group; the linker is an alkyne group; and the cationic moiety includes a protonated amine group, a sulfonium ion, a quaternary ammonium cation, or combinations thereof. In an example, the surface moiety is the alkyne group; the linker is an azide group; and the cationic moiety includes a protonated amine group, a sulfonium ion, a quaternary ammonium cation, or combinations thereof. In an example, a compound includes the positively chargeable moiety attached to the linker, and wherein the compound is propargyl choline bromide. In an example, the fluid includes a water. In an example, the temperature ranges from about 18° C. to about 60° C. and the time ranges from about 30 minutes to about 12 hours. In an example, the method further comprises adding a catalyst, a ligand, and a reducing agent to the flow cell with the fluid.

It is to be understood that any features of this method may be combined together in any desirable manner. Moreover, it is to be understood that any combination of features of this method and/or of the flow cell may be used together, and/or combined with any of the examples disclosed herein to achieve the benefits as described in this disclosure, including, for example, positive charges to attract and spatially confine library fragments.

A third aspect disclosed herein is a kit comprising a flow cell including a substrate; an initial polymeric hydrogel positioned on the substrate and having a surface moiety selected from the group consisting of a negatively chargeable atom, an azide group, and an alkyne group; and an amplification primer attached to the initial polymeric hydrogel; and a fluid including a positively chargeable moiety that is to interact or react with the surface moiety to form a cationic polymeric hydrogel including a cationic moiety.

It is to be understood that any features of the kit may be combined together in any desirable manner. Moreover, it is to be understood that any combination of features of any of the kit and/or the method and/or of the flow cell may be used together, and/or combined with any of the examples disclosed herein to achieve the benefits as described in this disclosure, including, for example, positive charges to attract and spatially confine library fragments.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 2A shows a portion of a flow cell including an initial polymeric hydrogel and FIG. 2B shows a portion of the flow cell including a positively charged (cationic) polymeric hydrogel;

FIG. 9A is an inverted micrograph image (where the original dark portions of the image have been inverted to white and the original light portions of the image have been inverted to black) of released DNA library fragments on a comparative flow cell including an untreated hydrogel in a single-lane of a glass substrate;

DETAILED DESCRIPTION

Figure 1:
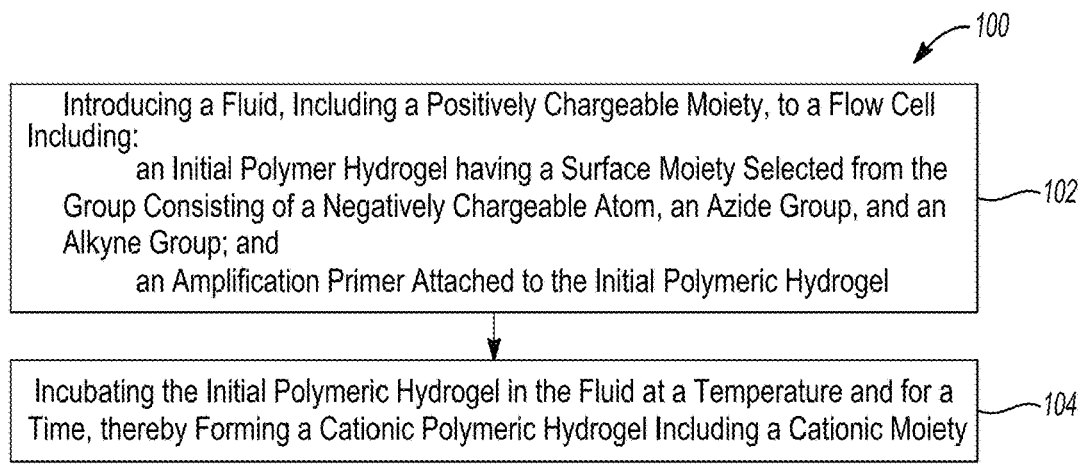
FIG. 1 is a flow diagram illustrating an example of a method disclosed herein.

Examples of the flow cell disclosed herein include positive charges and amplification primers at the surface of a polymeric hydrogel. The positive charges at the polymeric hydrogel surface help to attract and spatially confine library fragments that are released from a carrier that is subsequently introduced to the flow cell.

Library fragments are single-stranded, similarly sized (e.g., <1000 bp) deoxyribonucleic acid (DNA) pieces of a larger nucleic acid sample or complementary deoxyribonucleic acid (cDNA) pieces generated from ribonucleic acid (RNA) pieces of a larger nucleic acid sample, and the fragments have adapters attached at the respective ends. The positively charged hydrogel surface will attract negatively charged library fragments that are released from an individual carrier. This will reduce random binding of the library fragments across the flow cell surface and will reduce or prevent library fragments from seeding on the sidewalls of the flow cell. As such, the library seeding efficiency is improved.

Improved seeding efficiency may have many advantages and benefits. For example, library input requirement may be reduced when the seeding efficiency is improved. For another example, improved seeding efficiency can result in an at least substantially homogenized cluster density. During sequencing, individual clusters generate "spatial clouds" of fluorescence signals as nucleotides are incorporated into respective template strands of the clusters. The confinement of the clusters can at least reduce spatial cloud cross-talk and/or overlap, and can also improve the identification of spatial clouds. Still further, because the reads obtained from any individual cluster may be generated from the same sample, they may be used to reconstruct the sample by bioinformatically stitching the short reads together.

Examples of the method disclosed herein introduce the positive charges to the surface of an initial polymeric hydrogel, while maintaining the sequencing compatibility of the surface.

DEFINITIONS

Terms used herein will be understood to take on their ordinary meaning in the relevant art unless specified otherwise. Several terms used herein and their meanings are set forth below.

As used herein, the singular forms "a," "an," and "the" refer to both the singular as well as plural, unless the context clearly indicates otherwise. The term "comprising" as used herein is synonymous with "including," "containing," or "characterized by," and is inclusive or open-ended and does not exclude additional, unrecited elements or method steps.

Reference throughout the specification to "one example," "another example," "an example," and so forth, means that a particular element (e.g., feature, structure, composition, configuration, and/or characteristic) described in connection with the example is included in at least one example described herein, and may or may not be present in other examples. In addition, it is to be understood that the described elements for any example may be combined in any suitable manner in the various examples unless the context clearly dictates otherwise.

The terms "substantially" and "about" used throughout this disclosure, including the claims, are used to describe and account for small fluctuations, such as due to variations in processing. For example, these terms can refer to less than or equal to ±5% from a stated value, such as less than or equal to ±2% from a stated value, such as less than or equal to ±1% from a stated value, such as less than or equal to ±0.5% from a stated value, such as less than or equal to ±0.2% from a stated value, such as less than or equal to ±0.1% from a stated value, such as less than or equal to ±0.05% from a stated value.

Adapter. A linear oligonucleotide sequence that can be fused to a nucleic acid molecule, for example, by ligation or tagmentation. In some examples, the adapter is at least substantially non-complementary to the 3' end or the 5' end of any target sequence introduced to the flow cell. Suitable adapter lengths may range from about 10 nucleotides to about 100 nucleotides, or from about 12 nucleotides to about 60 nucleotides, or from about 15 nucleotides to about 50 nucleotides. The adapter may include any combination of nucleotides and/or nucleic acids. In some examples, the adapter includes one or more cleavable groups at one or more locations. In some examples, the adapter can include a sequence that is complementary to at least a portion of a primer, for example, a primer including a universal nucleotide sequence (such as a P5 or P7 sequence). In some examples, the adapter can include an index or barcode sequence that assists in downstream error correction, identification, or sequencing. The index may be unique to a sample or source of the nucleic acid molecule (e.g., a fragment). In some examples, the adapter can include a sequencing primer sequence or sequencing binding site. Combinations of different adapters may be incorporated into a nucleic acid molecule, such as a DNA fragment.

Capture site: A portion of a flow cell surface having been physically modified and/or modified with a chemical property that allows for localization of either a complex or a sample. In an example, the capture site may include a chemical capture agent.

Carrier. A hydrogel support that is capable of having a sequencing library contained therein or a solid support that is capable of having a sequencing-ready nucleic acid fragments attached to a surface thereof.

Chemical capture agent: A material, molecule or moiety that is capable of attaching, retaining, or binding to a target molecule (e.g., a complex or sample). One example chemical capture agent includes a capture nucleic acid (e.g., a capture oligonucleotide) that is complementary to at least a portion of a target nucleic acid of or attached to the target molecule. Another example chemical capture agent is a linking molecule. For a native DNA or RNA sample, the linking molecule may include a nucleic acid binding moiety on one end, such as intercalators that bind via charge or hydrophobic interaction. For a cell sample, the linking molecule may include a cell membrane binding moiety (e.g., antigens against surface proteins) or a membrane penetrating moiety (e.g., phospholipids on one end). Still another example chemical capture agent includes a member of a receptor-ligand binding pair (e.g., avidin, streptavidin, biotin, lectin, carbohydrate, nucleic acid binding protein, epitope, antibody, etc.) that is capable of binding to the target molecule (or to a linking moiety attached to the target molecule). Yet another example of the chemical capture agent is a chemical reagent capable of forming an electrostatic interaction, a hydrogen bond, or a covalent bond (e.g., thiol-disulfide exchange, click chemistry, Diels-Alder, etc.) with the target molecule.

Complex: A carrier, such as a hydrogel support or a solid support, and sequencing-ready nucleic acid fragments attached to or contained within the carrier. The carrier may also include one member of a binding pair whose other member is part of the capture site.

External immobilizing agent: A gaseous, liquid or viscous medium that is not miscible with a complex or sample that has been introduced to the flow cell lane(s) or chambers. The gaseous external immobilizing agent may be used to create a droplet around a complex or sample. An example of a gaseous external immobilizing agent is air that is directed at a suitable flow rate through the flow cell. For example, air may be used to aspirate a fluid containing a complex or sample from the flow cell, which forms droplets of the liquid containing the complex or sample. The formed droplet acts as a diffusion barrier. The liquid or viscous medium is used to prevent diffusion of a sequencing library released from a complex or formed within a chamber on a flow cell surface. The external immobilizing agent can form a diffusion barrier, as the sequencing libraries or any other polynucleotides have little to no solvation in the external immobilizing agent. Example external immobilizing agents in liquid form include hydrophobic oils, such as mineral oil, silicone oil, perfluorinated oil, a fluorinated carbon oil (e.g., FLUORINERT™ Electronic Liquid FC40 from 3M), or a combination thereof. Example external immobilizing agents in viscous medium form include buffers containing polymers (e.g., polyethylene glycol, polyvinylpyrrolidone, etc.), dextran, sucrose, glycerol, and the like. In some examples, the viscous medium is a temperature responsive gel. The temperature responsive gel is non-viscous at non-seeding temperatures, and turns into a viscous medium at seeding temperatures. Examples of temperature responsive gels include poly(N-isopropylacrylamide) and polyethylene oxide-polypropylene oxide-polyethylene oxide (PEO-PPO-PEO)/laponite nanoparticle composites.

Fragment: A portion or piece of genetic material (e.g., DNA, RNA, etc.).

Hydrogel or hydrogel matrix: A semi-rigid polymeric material that is permeable to liquids and gases. The polymeric material that forms the hydrogel may be linear or lightly cross-linked via covalent, ionic, or hydrogen bonds. In an example, the hydrogel includes from about 60% to about 90% fluid, such as water, and from about 10% to about 30% polymer. The hydrogel may be porous, i.e., including open/void space. The porosity is a fractional volume (dimensionless) of the hydrogel, i.e., measures void space in a material and is a fraction of the volume of voids over the total volume, as a percentage between 0 and 100% (or a fraction between 0 and 1). In an example, the porosity of the hydrogel may range from about 50% (0.5) to about 99% (0.99). The porosity may be sufficient to allow diffusion of reagents (e.g., enzymes, chemicals, and smaller sized oligonucleotides (less than 50 base pairs, e.g., primers), but prohibits diffusion of larger sized nucleic acid molecules (e.g., samples, fragments, etc.).

The term "cationic polymeric hydrogel," as used herein, refers to the initial polymerized hydrogel having a cationic moiety i) integrated into one of the monomeric units or ii) attached to one of the monomeric units through a linker. The term "initial polymeric hydrogel," as used herein, refers to the polymerized hydrogel prior to any reaction/interaction to introduce the cationic moiety. The cationic polymeric hydrogel may also be referred to herein as a positively charged hydrogel.

Hydrogel support: A hydrogel having an at least substantially spherical shape (e.g., a hydrogel bead) that can contain a sequencing library therein.

Nucleic acid molecule: A polymeric form of nucleotides of any length, and may include ribonucleotides, deoxyribonucleotides, analogs thereof, or mixtures thereof. The term may refer to single stranded or double stranded polynucleotides.

A "target" or "template" nucleic acid molecule may refer to a sequence that is to be analyzed.

The nucleotides in a nucleic acid molecule may include naturally occurring nucleic acids and functional analogs thereof. Examples of functional analogs are capable of hybridizing to a nucleic acid in a sequence specific fashion or capable of being used as a template for replication of a particular nucleotide sequence. Naturally occurring nucleotides generally have a backbone containing phosphodiester bonds. An analog structure can have an alternate backbone linkage including any of a variety known in the art. Naturally occurring nucleotides generally have a deoxyribose sugar (e.g., found in DNA) or a ribose sugar (e.g., found in RNA). An analog structure can have an alternate sugar moiety including any of a variety known in the art. Nucleotides can include native or non-native bases. A native DNA can include one or more of adenine, thymine, cytosine and/or guanine, and a native RNA can include one or more of adenine, uracil, cytosine and/or guanine. Any non-native base may be used, such as a locked nucleic acid (LNA) and a bridged nucleic acid (BNA).

Positively Chargeable Moiety: A positively chargeable moiety may be any functional group that carries or can carry a positive charge. In an example, the positive charge may be introduced to the chargeable moiety through a displacement reaction. In other examples, the positively chargeable moiety carries a positive charge at a particular pH (e.g., a physiological pH).

Primer. A nucleic acid molecule that can hybridize to a target sequence of interest. In an example, the primer functions as a substrate onto which nucleotides can be polymerized by a polymerase. For example, an amplification or capture primer can serve as a starting point for template amplification and cluster generation. In another example, a synthesized nucleic acid strand may include a site to which a primer (e.g., a sequencing primer) can hybridize in order to prime synthesis of a new strand that is complementary to the synthesized nucleic acid strand. Any primer can include any combination of nucleotides or analogs thereof. In some examples, the primer is a single-stranded oligonucleotide or polynucleotide. The primer length can be any number of bases long and can include a variety of non-natural nucleotides. In an example, the sequencing primer is a short strand, ranging from 10 to 60 bases, or from 20 to 40 bases.

Sample: Any source of genetic material, such as cells, microbiomes, or nucleic acids. In some examples, the cell is a single cell including a prokaryotic or a eukaryotic cell. In some examples, the cell is a mammalian cell, a human cell, or a bacterial cell. In some examples, the nucleic acid is a long DNA molecule, including viral nucleic acids, bacterial nucleic acids, or mammalian nucleic acids. In some examples, the sample is bound (as fragments) via insertion of transposons bound to the surface of a solid support (e.g., bead).

Sequencing-ready nucleic acid fragments: A portion (fragment) of genetic material having adapters at the 3' and 5' ends. In the sequencing-ready nucleic acid fragment, each adapter includes a known universal sequence (e.g., which is complementary to at least a portion of a primer on a flow cell) and a sequencing primer sequence. Both of the adapters may also include an index (barcode or tag) sequence. In an example, one side (e.g., the P5 side) may contain a bead (or other solid support) index and the other side (e.g., the P7 side) may contain a sample index. A sequencing-ready nucleic acid fragment may be bound via insertion of transposons to the surface of a solid support (e.g., bead), or directly immobilized through a binding pair or other cleavable linker. A sequencing-ready nucleic acid fragment may also be contained within a hydrogel support.

Seeding: Immobilization of adapted fragments (e.g., sequencing-ready nucleic acid fragments) on a hydrogel of an example of the flow cells disclosed herein.

Sequencing library: A collection of nucleic acid fragments of one or more target nucleic acid molecules, or amplicons of the fragments. In some examples, the fragments are linked to one or more adapters at their 3' and 5' ends. In some examples, a sequencing library is prepared from one or more target nucleic acid molecules and is part of a complex.

Solid support: A small body made of a rigid or semi-rigid material having a shape characterized, for example, as a sphere, oval, microsphere, or other recognized particle shape whether having regular or irregular dimensions. The solid support can have a sequencing library attached thereto. Example materials that are useful for the solid support include, without limitation, glass; plastic, such as acrylic, polystyrene or a copolymer of styrene and another material, polypropylene, polyethylene, polybutylene, polyurethane or polytetrafluoroethylene (TEFLON® from The Chemours Co); polysaccharides or cross-linked polysaccharides such as agarose or Sepharose; nylon; nitrocellulose; resin; silica or silica-based materials including silicon and modified silicon; carbon-fiber, metal; inorganic glass; optical fiber bundle, or a variety of other polymers. Example solid supports include controlled pore glass beads, paramagnetic beads, thoria sol, Sepharose beads, nanocrystals and others known in the art as described, for example, in Microsphere Detection Guide from Bangs Laboratories, Fishers Ind.

Tagmentation: Modification of a nucleic acid molecule (e.g., a DNA or RNA sample) by a transposome to fragment the nucleic acid molecule and ligate adapters to the 5' and 3' ends of the fragment in a single step. Tagmentation reactions may be used to prepare sequencing libraries, in particular, complexes that include the solid support. Tagmentation reactions combine random sample fragmentation and adapter ligation into a single step, which increases the efficiency of the sequencing library preparation process.

Transposome: An integration enzyme (e.g., an integrase or a transposase) and a nucleic acid including an integration recognition site (e.g., a transposase recognition site).

Universal nucleotide sequence: A region of a sequence that is common to two or more nucleic acid molecules, where the molecules also have regions that differ from each other. A universal sequence that is present in different members of a collection of molecules can allow for the capture of several different nucleic acids using a population of universal capture nucleic acids (i.e., the adapter that has a sequence that is complementary to at least a portion of a primer). Similarly, a universal sequence that is present in different members of a collection of molecules can allow for the amplification or replication of several different nucleic acids using a population of universal sequencing binding sites (sequencing primer sequences).

Method for Making a Positively Charged Flow Cell Surface

An example of a method 100 for forming an example of a flow cell is shown in FIG. 1. As depicted, one example of the method 100 includes introducing a fluid, including a positively chargeable moiety, to a flow cell including an initial polymeric hydrogel having a surface moiety selected from the group consisting of a negatively chargeable atom, an azide group, and an alkyne group, and an amplification primer attached to the initial polymeric hydrogel (reference numeral 102); and incubating the initial polymeric hydrogel in the fluid at a temperature and for a time, thereby forming a cationic polymeric hydrogel including a cationic moiety (reference numeral 104).

Figure 2A:
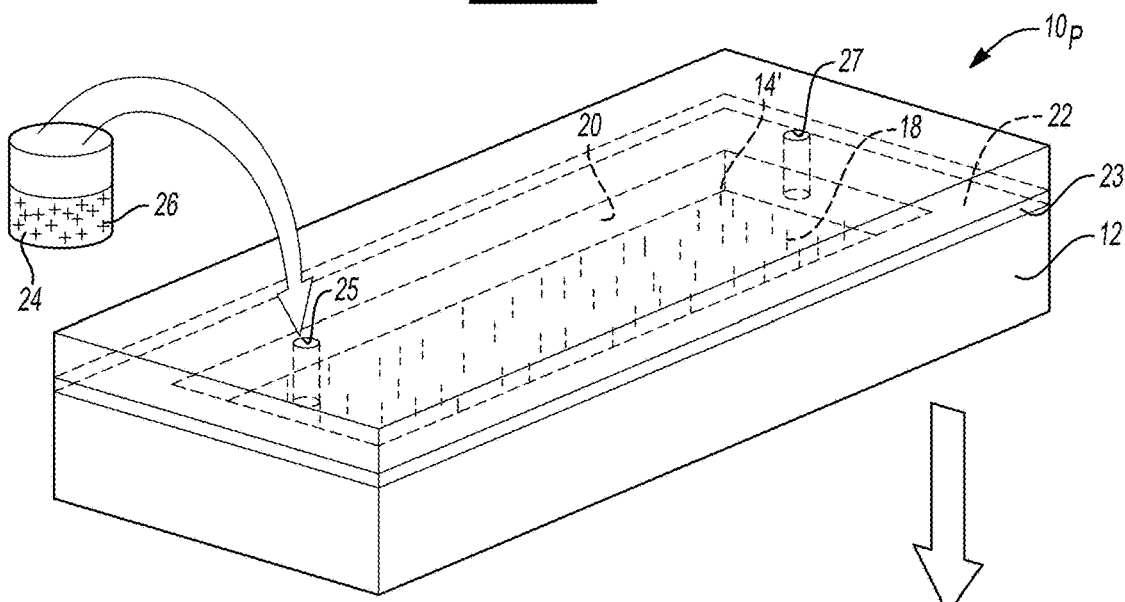
FIGS. 2A and 2B are semi-schematic, perspective views which together illustrate the method of FIG. 1, where
Figure 2B:
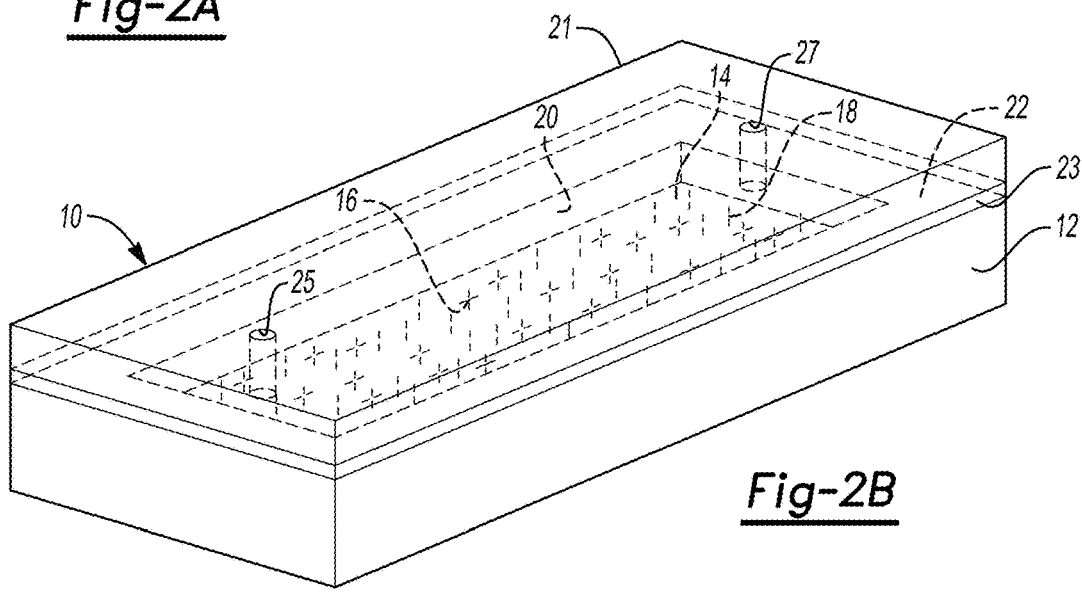

The method 100 is also schematically shown in FIG. 2A and FIG. 2B.

As shown in FIG. 2A, at the outset of the method 100, the flow cell 10p (which is a precursor to the flow cell 10 shown in FIG. 2B) includes a substrate 12, an initial polymeric hydrogel 14' on the substrate 12, and an amplification primer 18 attached to the initial polymeric hydrogel 14'.

The substrate 12 is generally rigid and is insoluble in an aqueous liquid. Examples of suitable substrates 12 include epoxy siloxane, polyhedral oligomeric silsequioxanes (POSS) or derivatives thereof, glass, modified glass, plastics, nylon, ceramics/ceramic oxides, silica (silicon oxide ($SiO_2$)), fused silica, silica-based materials, aluminum silicate, silicon, modified silicon (e.g., boron doped p+ silicon), silicon nitride ($Si_3N_4$), tantalum pentoxide ($TaO_5$) or other tantalum oxide(s) ($TaO_x$), hafnium oxide ($HfO_2$), inorganic glasses, or the like. An example of POSS can be that described in Kehagias et al., Microelectronic Engineering 86 (2009), pp. 776-778, which is incorporated by reference in its entirety. Some examples of suitable plastics for the substrate 12 include acrylics, polystyrene, copolymers of styrene and other materials, polypropylene, polyethylene, polybutylene, polyurethanes, polytetrafluoroethylene (such as TEFLON® from The Chemours Co.), cyclic olefins/cyclo-olefin polymers (COP) (such as ZEONOR® from Zeon), polyimides, etc. The substrate 12 may also be glass or silicon or POSS, with a coating layer of tantalum oxide or another ceramic oxide at the surface. Another example of a suitable substrate 12 is a silicon-on-insulator substrate.

The form of the substrate 12 may be a wafer, a panel, a rectangular sheet, a die, or any other suitable configuration. In an example, the substrate 12 may be a circular wafer or panel having a diameter ranging from about 2 mm to about 300 mm. As a more specific example, the substrate 12 is a wafer having a diameter ranging from about 200 mm to about 300 mm. In another example, the substrate 12 may be a rectangular sheet or panel having its largest dimension up to about 10 feet (~3 meters). As a specific example, the substrate 12 is a die having a width ranging from about 0.1 mm to about 10 mm. While example dimensions have been provided, it is to be understood that a substrate 12 with any suitable dimensions may be used.

The substrate 12 shown in FIG. 2A has a lane 20 defined therein. The lane 20 may be defined in the substrate 12 using any suitable technique that depends, in part, upon the material(s) of the substrate 12. In one example, the lane 20 is etched into a glass substrate 12. In another example, the lane 20 may be patterned into a resin substrate 12 using photolithography, nanoimprint lithography, etc. In still another example, a separate material (not shown) may be applied to the substrate 12 so that the separate material defines the walls of the lane 20 and the substrate 12 defines the bottom of the lane 20.

In an example, the lane 20 has a rectilinear configuration. The length and width of the lane 20 may be smaller, respectively, than the length and width of the substrate 12 so that portion of the substrate surface 22 surrounding the lane 20 is available for bonding to a lid 21. In some instances, the width of each lane 20 can be at least about 1 mm, at least about 2.5 mm, at least about 5 mm, at least about 7 mm µm, at least about 10 mm, or more. In some instances, the length of each lane 20 can be at least about 10 mm, at least about 25 mm, at least about 50 mm, at least about 100 mm, or more. The width and/or length of each lane 20 can be greater than, less than or between the values specified above. In an example, the lane 20 is square (e.g., 10 mm×10 mm).

The depth of each lane 20 can be a monolayer thick when microcontact, aerosol, or inkjet printing is used to deposit a separate material that defines the lane walls. For other examples, the depth of each lane 20 can be about 1 µm, about 10 µm, about 50 µm, or more. In an example, the depth may range from about 10 µm to about 30 µm. In addition to the positively charged polymeric hydrogel that attracts the released library fragments, this depth may help to block lateral diffusion of released library fragments between adjacent lanes 20, e.g., when multiple lanes 20 are used. In another example, the depth is about 5 µm or less. It is to be understood that the depth of each lane 20 be greater than, less than or between the values specified above.

While a single lane 20 is shown in FIG. 2A, it is to be understood that the substrate 12 may include multiple lanes (e.g., 2, 3, 4, 8, etc.) that are fluidically separate from each other.

In the example shown in FIG. 2A, the lane 20 has the initial polymeric hydrogel 14' therein. Prior to integration or attachment of the cationic moiety 16 (FIG. 2B), the hydrogel may be referred to as the initial polymeric hydrogel 14' (see FIG. 2A). After integration or attachment of the cationic moiety 16, the hydrogel may be referred to as the cationic polymeric hydrogel 14 (see FIG. 2B).

The initial polymeric hydrogel 14' may be a copolymer of at least two different monomeric units. The initial polymeric hydrogel 14' may be represented by: $(M1)_n(M2)_m$, where M1 is the first monomeric unit, M2 is the second monomeric unit, n is an integer ranging from 1 to 50,000 and m is an integer ranging from 1 to 100,000. In the cationic polymeric hydrogel 14, M1 may be replaced with M1' (described in reference to FIG. 3) or M1" (described in reference to FIG. 4), but M2, n, and m are the same as described for the initial polymeric hydrogel 14'. Examples of each of the monomeric unis M1, M2 will now be described in more detail.

One of the monomeric units M1 includes a surface moiety selected from the group consisting of a negatively chargeable atom, an azide group, and an alkyne group. The negatively chargeable atom may be any group that is easily displaced, such as a relatively weak nucleophile. Some specific examples of the negatively chargeable atom include a halogen, such as bromine, iodine, etc.

Each of these surface moieties of the monomeric unit M1 is capable of being displaced by or covalently attaching to an amplification primer 18. For example, bromine is capable of being displaced by a phospho-thioate group on the 5' end of a primer 18. For another example, an azide group is capable of covalently linking to an alkyne group on the 5' end of a primer 18. For still another example, an alkyne group is capable of covalently linking to an azide group on the 5' end of a primer 18.

Each of these surface moieties of the monomeric unit M1 can also enable the attachment of the cationic moiety 16 to the initial polymeric hydrogel 14' to generate the cationic polymeric hydrogel 14.

In some examples, the surface moiety of the monomeric unit M1 is displaced by the cationic moiety 16, and thus the cationic moiety 16 becomes integrated into the monomeric unit M1. In other words, the cationic moiety 16 attaches to the monomeric unit M1 in the same position that the surface moiety had been attached. For example, the surface moiety may be a weaker redox species than the cationic moiety 16, and a displacement reaction may take place where the surface moiety is swapped out for the cationic moiety 16. An example of the displaceable surface moiety is the negatively chargeable atom, such as bromine.

In other examples, the surface moiety reacts with a linker to attach the cationic moiety 16 to the monomeric unit M1. For example, an azide group is capable of covalently linking to a terminal alkyne group of a linker. For still another example, an alkyne group is capable of covalently linking to a terminal azide group of a linker.

Because of the multi-functionality of the surface moiety of the monomeric unit M1, it is to be understood that the some of the surface moieties of the monomeric unit M1 will attach amplification primers 18 and some of the surface moieties will be displaced by, or will attach to the cationic moiety 16. In some instances, the amount of amplification primers 18 that are attached range from about 10 times to about 50 times more that the amount of cationic moieties 16 that are attached.

Any monomeric unit M1 that includes the surface moiety disclosed herein and that can co-polymerize with the other monomeric unit(s) M2 may be used to form the initial polymeric hydrogel 14'. In an example, the monomeric unit M1 (including the surface moiety) also includes an acrylamide unit:

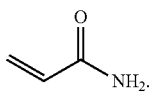

Variations of the acrylamide unit may also be used, for example, the carbon in the alkene can be optionally substituted or the N can be optionally substituted. Examples of other acrylamide units include methacrylamide, N,N-dimethylacrylamide, ethylacrylamide, etc.

One specific example of the monomeric unit M1 that includes both the acrylamide unit and bromine as the negatively chargeable atom is N-(5-bromoacetamidylpentyl) acrylamide (brapa):

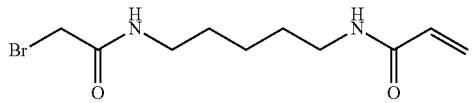

Variations of N-(5-bromoacetamidylpentyl) acrylamide may also be used, for example, the alkyl chain —(CH$_2$)— may range from 1 to 50 and/or each of the —(CH$_2$)— can be optionally substituted.

One specific example of the monomeric unit M1 that includes both the acrylamide unit and the azide group is N-(5-azidoacetamidylpentyl) acrylamide:

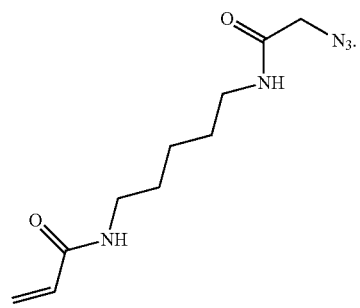 [SMILES: C=CC(=O)NCCCCCNC(=O)CN=[N+]=[N-]]

Variations of N-(5-azidoacetamidylpentyl) acrylamide may also be used, for example, the alkyl chain —(CH$_2$)— may range from 1 to 50 and/or each of the —(CH$_2$)— can be optionally substituted. Another example of the monomeric unit M1 that includes both the acrylamide unit and the azide group is represented by:

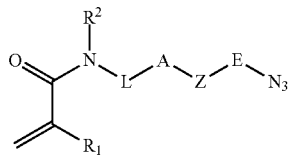

wherein $R_1$ is H or C1-C4 alkyl; $R^2$ is H or C1-C4 alkyl; L is a linking group including a linear chain with 2 to 20 atoms selected from the group consisting of carbon, oxygen, and nitrogen and optional substituents on the carbon and any nitrogen atoms in the chain; E is a linear chain including 1 to 4 atoms selected from the group consisting of carbon, oxygen and nitrogen, and optional substituents on the carbon and any nitrogen atoms in the chain; A is an N substituted amide with an H or C1-C4 alkyl attached to the N; and Z is a nitrogen containing heterocycle. Examples of Z include 5 to 10 ring members present as a single cyclic structure or a fused structure. Still another example of the monomeric unit M1 that includes both the acrylamide unit and the azide group is represented by:

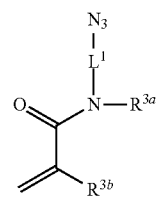

wherein $R^{3a}$ is selected from hydrogen, optionally substituted alkyl, optionally substituted phenyl, or optionally substituted C7-C14 aralkyl; $R^{3b}$ is selected from hydrogen, optionally substituted alkyl or optionally substituted phenyl; and $L^1$ is selected from an optionally substituted alkylene linking group or an optionally substituted heteroalkylene linking group.

One specific example of the monomeric unit M1 that includes both the acrylamide unit and the alkyne group is N-propargylacrylamide:

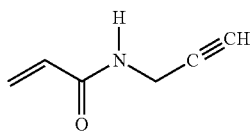

It is to be understood that other monomeric units M1 may be used to form the initial polymeric hydrogel 14', as long as they are functionalized with one the surface moieties disclosed herein.

Any of the monomeric units M1 may be copolymerized with the second monomeric unit M2 to form the initial polymeric hydrogel 14'. Examples of the second monomeric unit M2 include an acrylamide unit, an N,N-dimethylacrylamide unit:

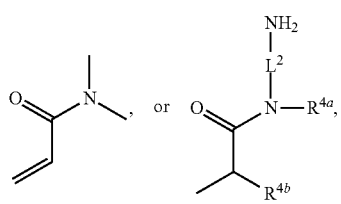

wherein $R^{4a}$ is selected from hydrogen, optionally substituted alkyl, optionally substituted phenyl, or optionally substituted C7-C14 aralkyl; $R^{4b}$ is selected from hydrogen, optionally substituted alkyl or optionally substituted phenyl; and $L^2$ is selected from an optionally substituted alkylene linking group or an optionally substituted heteroalkylene linking group. The second monomer unit M2 does not include the surface moiety (e.g., the negatively chargeable atom, the azide group, or the alkyne group) of the first monomer unit M1.

In still other examples, the monomeric unit M1 may be copolymerized with both an acrylamide unit (e.g., monomeric unit M2) and an N,N-dimethylacrylamide (e.g., monomeric unit M3) to form the initial polymeric hydrogel 14'. In these examples, the initial polymeric hydrogel 14' may be represented by $(M1)_n(M2)_m(M3)_q$, where n is an integer ranging from 1 to 50,000, m is an integer ranging from 1 to 100,000, and q is an integer ranging from 1 to 100,000. In the corresponding cationic polymeric hydrogel 14, M1 may be replaced with M1' (described in reference to FIG. 3) or M1" (described in reference to FIG. 4), but M2, M3, n, m, and q are the same as described for the initial polymeric hydrogel 14'.

In some examples, the initial polymeric hydrogel 14' (either $(M1)_n(M2)_m$ or $(M1)_n(M2)_m(M3)_q$) (and the corresponding cationic polymeric hydrogel 14) may be a linear copolymer or a lightly cross-linked copolymer. The molecular weight of the initial polymeric hydrogel 14' may range from about 10 kDa to about 1500 kDa, or may be, in specific examples, about 312 kDa or about 500 kDa. The molecular weight of the cationic polymeric hydrogel 14 may be higher than its corresponding initial polymeric hydrogel 14' depending upon the cationic moiety 16 that is integrated therein or the cationic moiety 16 and linker that are attached thereto.

One of ordinary skill in the art will recognize that the arrangement of the recurring "n" and "m" or "n," "m," and "q" features are representative, and the monomeric subunits may be present in any order in the initial polymeric hydrogel 14'/cationic polymeric hydrogel 14 structure (e.g., random, block, patterned, or a combination thereof).

To introduce the initial polymeric hydrogel 14' into the lane 20, a mixture of the copolymer (either $(M1)_n(M2)_m$ or $(M1)_n(M2)_m(M3)_q$) may be generated and then applied to the substrate 12. In one example, the copolymer may be present in a mixture (e.g., with water or with ethanol and water). The copolymer mixture may then be applied to the substrate surface(s) 22 using spin coating, or dipping or dip coating, or flow of the material under positive or negative pressure, or another suitable technique.

In some examples, the substrate surface 22 (including the portion that is exposed in the lane 20) may be activated, and then the copolymer mixture may be applied thereto. In one example, a silane or silane derivative (e.g., norbornene silane) may be deposited on the substrate surface 22 using vapor deposition, spin coating, or other deposition methods. In another example, the substrate surface 22 may be exposed to plasma ashing to generate surface-activating agent(s) (e.g., —OH groups) that can adhere to the copolymer. In still other examples, plasma ashing followed by silanization may be used to activate the substrate surface 22.

Depending upon the copolymer, the applied mixture may be exposed to a curing process to form the initial (covalently bonded) polymeric hydrogel 14' across the surface 22. In an example, curing may take place at a temperature ranging from room temperature (e.g., about 25° C.) to about 95° C. for a time ranging from about 1 millisecond to about several days. Polishing may then be performed in order to remove the initial polymeric hydrogel 14' from the surface 22 at the perimeter of the substrate 12, while leaving the initial polymeric hydrogel 14' on the surface 22 in the lane 20 at least substantially intact.

The flow cell 10p also includes the amplification primer 18.

A grafting process may be performed to graft the amplification primers 18 to the initial polymeric hydrogel 14' in the lane 20. In an example, the amplification primers 18 can be immobilized to the initial polymeric hydrogel 14' by single point covalent attachment at or near the 5' end of the primers 18. This attachment leaves i) an adapter-specific portion of the primers 18 free to anneal to its cognate sequencing-ready nucleic acid fragment and ii) the 3' hydroxyl group free for primer extension. Any suitable covalent attachment may be used for this purpose. Examples of terminated primers that may be used include alkyne terminated primers (e.g., which may attach to the azide surface moiety of the initial polymeric hydrogel 14'), phospho-thioate terminated primers (e.g., which may attach to the bromine surface moiety of the initial polymeric hydrogel 14'), or azide terminated primers (e.g., which may attach to the alkyne surface moiety of the initial polymeric hydrogel 14'). Specific examples of suitable primers 18 include P5 and P7 primers used on the surface of commercial flow cells sold by Illumina Inc. for sequencing on HISEQ™, HISEQX™, MISEQ™, MISEQDX™, MINISEQ™, NEXTSEQ™, NEXTSEQDX™, NOVASEQ™, GENOME ANALYZER™, ISEQ™, and other instrument platforms.

In an example, grafting may involve flow through deposition (e.g., using a temporarily bound or permanently bonded lid 21), dunk coating, spray coating, puddle dispensing, or by another suitable method that will attach the primer(s) 18 to the initial polymeric hydrogel 14' in the lane 20. Each of these example techniques may utilize a primer solution or mixture, which may include the primer(s), water, a buffer, and a catalyst. With any of the grafting methods, the primers 18 react with reactive groups (e.g., the surface moiety of monomeric unit M1) of the initial polymeric hydrogel 14' in the lane 20, and have no affinity for the surrounding substrate 12. As such, the primers 20 selectively graft to the initial polymeric hydrogel 14' in the lane 20.

The concentration of the primers 18 in the primer solution or mixture may be such that some of the surface moieties of the monomeric unit M1 of the initial polymeric hydrogel 14' remain available for interaction or reaction to introduce the cationic moieties 16 (FIG. 2B).

As shown in FIG. 2A, a fluid 24, including a positively chargeable moiety 26, is introduced to the flow cell $10_P$. The initial polymeric hydrogel 14' is allowed to incubate in the fluid 24 at a temperature and for a time that is sufficient to form the cationic polymeric hydrogel 14 including a cationic moiety 16 (shown in FIG. 2B).

The fluid 24 and the positively chargeable moiety 26 that are used may depend upon the initial polymeric hydrogel 14', and in particular, upon the surface moiety of the monomeric unit M1 in the initial polymeric hydrogel 14'. The incubation temperature and time may also depend upon the positively chargeable moiety 26 and the initial polymeric hydrogel 14'.

Some examples of the positively chargeable moiety 26 integrate themselves into the monomeric unit M1 of the initial polymeric hydrogel 14' to form the cationic polymeric hydrogel 14 including the cationic moiety 16. When the cationic moiety 16 is "integrated into the monomeric unit of the initial polymeric hydrogel," it is meant that the cationic moiety 16 has displaced the surface moiety of the monomeric unit M1 of the initial polymeric hydrogel 14'. In this example, the surface moiety is the negatively chargeable atom and the positively chargeable moiety 26 is a redox species that is stronger than the negatively chargeable atom. As examples, the negatively chargeable atom of the monomeric unit M1 is bromine and the positively chargeable moiety is selected from the group consisting of tris(hydroxymethyl)phosphine, tris(hydroxypropyl)phosphine, tetrakis(hydroxymethyl)phosphine, and tris(2-carboxyethyl) phosphine. Any of these phosphine positively chargeable moieties can displace the bromine atom of the monomeric unit M1 of the initial polymeric hydrogel 14', such that a corresponding phosphonium cation becomes part of the monomeric unit M1' (see FIG. 3) of the cationic polymeric hydrogel 14. Table 1 illustrates the positively chargeable moiety 26 used in the displacement reaction of bromine, and the corresponding cation that is integrated into the monomeric unit M1' of the cationic polymeric hydrogel 14. In each of these examples, the counter ion is bromide (Br⁻).

TABLE 1

| positively chargeable moiety | corresponding cation |
|---|---|
| tris(hydroxymethyl)phosphine | tris(hydroxymethyl)phosphonium cation |
| tris(hydroxypropyl)phosphine | tris(hydroxypropyl)phosphonium cation |
| tetrakis(hydroxymethyl)phosphine | tetrakis(hydroxymethyl)phosphonium cation |
| tris(2-carboxyethyl)phosphine | tris(2-carboxyethyl)phosphonium cation |

Figure 3:
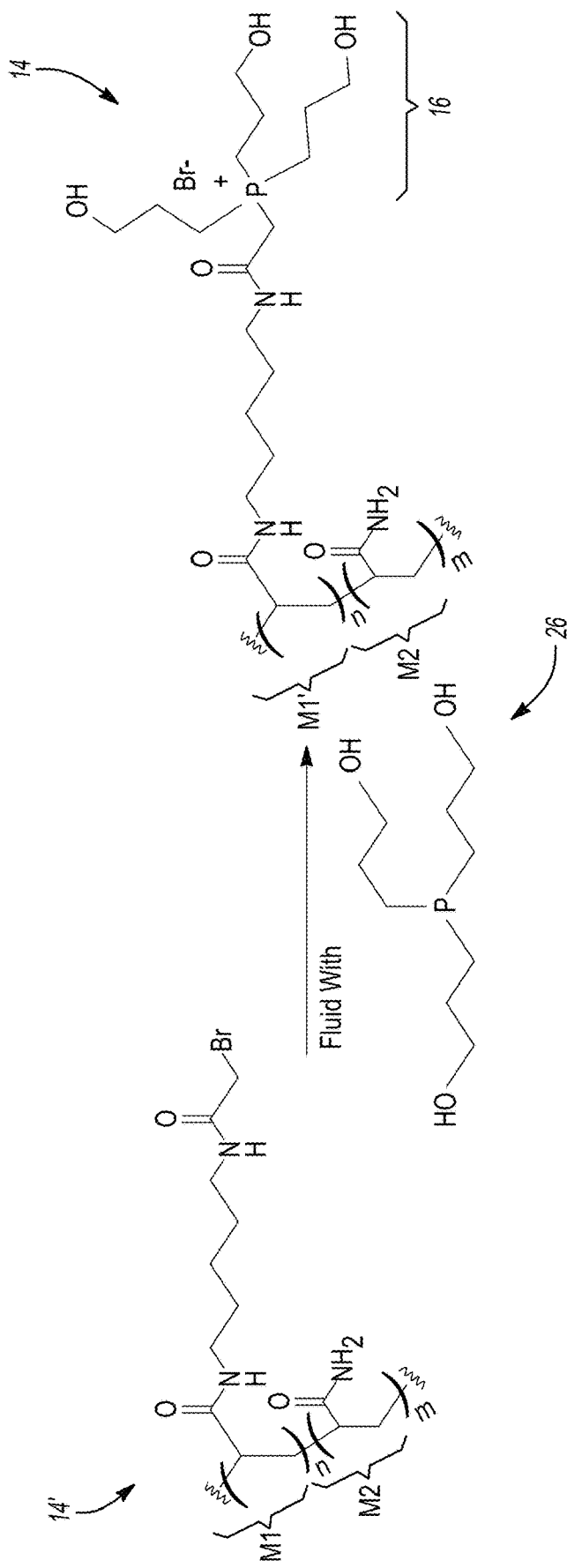
FIG. 3 is a chemical formula illustrating the formation of one example of a cationic polymeric hydrogel.

An example of the displacement reaction is shown in FIG. 3. In this example, the initial polymeric hydrogel 14' is a silane free acrylamide including N-(5-bromoacetamidylpentyl) acrylamide as the first monomeric unit M1 and acrylamide as the second monomeric unit M2. When exposed to the fluid 24 including the positively chargeable moiety 26 (which, in this example, is tris(hydroxypropyl)phosphine), the positively chargeable moiety 26 displaces the negatively chargeable atom of the initial polymeric hydrogel 14'. The result of the displacement reaction is the cationic polymeric hydrogel 14, which includes the cationic moiety 16 (which, in this example, is a tris(hydroxypropyl)phosphonium cation) attached to the monomeric unit M1' where the bromine had been attached to the monomeric unit M1.

In the example shown in FIG. 3, the fluid 24 may include a buffer having a pH ranging from 6 to 12. As examples, the buffer may be a tris buffer or an ethanolamine buffer. A concentration of the positively chargeable moiety 26 in the fluid 24 may range from about 1 mM to about 500 mM. In an example, the concentration of the positively chargeable moiety 26 in the fluid 24 may range from about 50 mM to about 400 mM. In another example, the concentration of any of the phosphine positively chargeable moieties 26 in the fluid 24 may be about 100 mM.

In this example, the incubation temperature ranges from about 18° C. to about 65° C. and the incubation time ranges from about 1.5 minutes to about 5 minutes.

It is to be understood that the example reaction shown in FIG. 3 is one example of the displacement reaction, and that other monomeric units M1 (e.g., including another displaceable surface moiety), M2 and/or other positively chargeable moieties 26 may be used.

Other examples of the positively chargeable moiety 26 attach to the monomeric unit M1 of the initial polymeric hydrogel 14' through a linker 28 (FIG. 4) to form the cationic polymeric hydrogel 14 including the cationic moiety 16. When the cationic moiety 16 is "attached to the monomeric unit of the polymeric hydrogel through a linker," it is meant that the surface moiety of the monomeric unit M1 of the initial polymeric hydrogel 14' reacts with a linker 28 to attach the cationic moiety 16.

In this example, the surface moiety is the azide group or the alkyne group, and the positively chargeable moiety 26 covalently attaches to the surface moiety through the linker 28. In one example, the surface moiety (of the monomeric unit M1) includes a terminal azide group and the linker 28 includes an alkyne group. In another example, the surface moiety (of the monomeric unit M1) includes a terminal alkyne group and the linker 28 includes an azide group.

In addition to the azide group or the alkyne group, the linker 28 may also include a chain, which may be a single —CH₂— unit, may include several —CH₂— units, several CH₂CH₂O— units, an oligonucleotide chain, or another polymeric chain. In one example, the linker 28 is a bi-functional DNA oligo. By "bi-functional", it is meant that one end of the DNA oligo linker has one end group that can attach to the initial polymeric hydrogel 14' and another end group that can attach to the cationic moiety 16.

Any example of the linker 28 may also be cleavable. By "cleavable", it is meant that the linker 28 includes a cleavable bond, and thus the cationic moiety 16 can be removed from the flow cell surface. As examples, the linker 28 may include a cleavable disulfide bond, a photocleavable bond, a cleavable phosphodiester bond, or combinations thereof. As one example, the phosphodiester bonds of the DNA oligo may be cleaved via enzymatic cleavage. As other examples, the linker 28 may include a cleavable disulfide bond (S—S) or a photocleavable bond (e.g., linkers including a nitrobenzyl group, such as the photo-cleavable spacer:

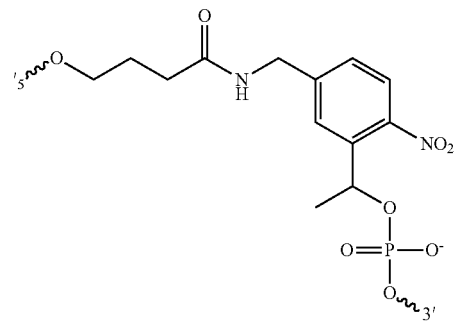

(available from Integrated DNA Technologies). In an example, cleavable bond is positioned between the terminal azide or alkyne group and the positively chargeable moiety 26. A cleavable bond in the linker 28 may be desirable so that the cationic moiety 16 may be removed from the cationic polymeric hydrogel 14, for example, after the library fragments are seeded, after DNA is extracted from a lysate, etc. Cleavage of the cationic moiety 16 would remove the positive charges, and the flow cell surface would revert to its initial charge state (e.g., the charge prior to introduction of the cationic moiety 16).

In this example, the positively chargeable moiety 26 may be any group that carries or can carry a positive charge, and that can attach to the linker 28. As examples, the positively chargeable moiety 26 may be an amine group, such as polylysine, polyamidoamine, etc. that can carry a positive charge at a physiological pH (resulting in a protonated amine group: R—$NH_3^+$ as the cationic moiety 16), or a quaternary ammonium salt, which can carry a positive charge at most pHs (resulting in a quaternary ammonium cation:

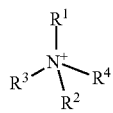

as the cationic moiety 16), or a sulfonium ion:

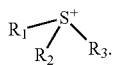

In some examples, the initial polymeric hydrogel 14' may include combinations of different positively chargeable moieties 26.

In some examples, the positively chargeable moiety 26 is attached to the linker 28, and the resulting compound 30 (FIG. 4) is incorporated into the fluid 24 that is introduced to the flow cell 10$_P$ to generate the cationic polymeric hydrogel 14. These compounds 30 may be commercially available or may be synthesized. As examples of suitable compounds 30, the azide-containing or alkyne-containing linker 28 may be attached to any one of the R groups of an amine group, a quaternary ammonium group, or a sulfonium ion. One example of the compound 30 is propargyl choline bromide:

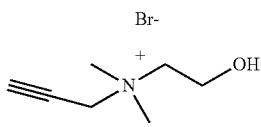

which includes the alkyne linker 28 attached to the N,N,N-trimethylethanolammonium cation (which is in the choline class of quaternary ammonium cations). Other examples of the compound 30 include azidoethyl-SS-ethylamine:

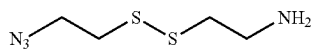

which includes an azide-containing linker 28 attached to an amine group (which can form a protonated amine), or propargyl-SS-ethylamine:

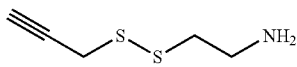

which includes an alkyne-containing linker 28 attached to an amine group (which can form a protonated amine). These two particular linkers 28 include the azide group ($N_3$) or the alkyne group (C≡C) as well as a cleavable disulfide bond (S—S) in an alkyl chain.

Figure 4:
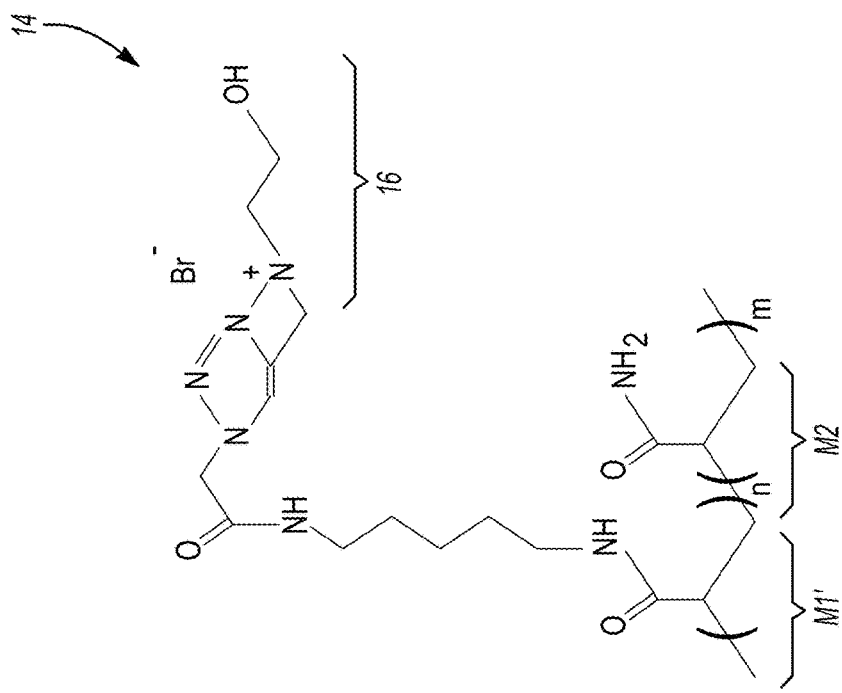
FIG. 4 is a chemical formula illustrating the formation of another example of a cationic polymeric hydrogel.
Figure 4:
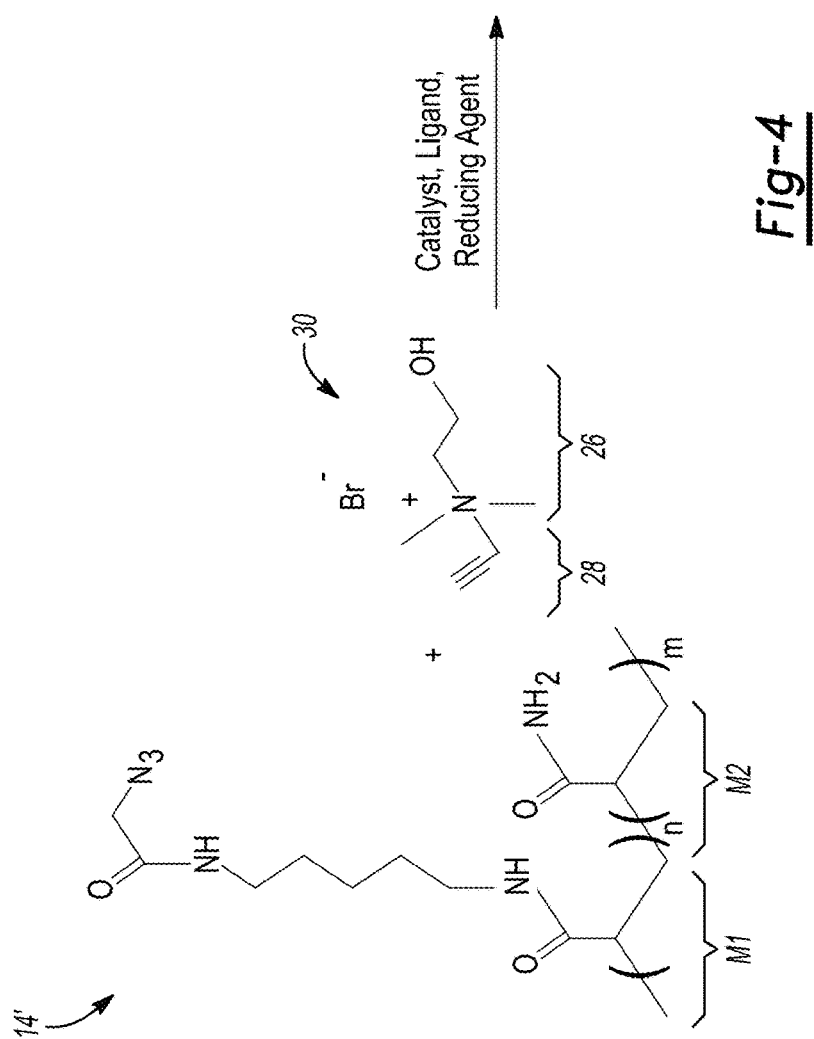

An example of utilizing the linker 28 to attach the positively chargeable moiety 26 to the initial polymeric hydrogel 14' is shown in FIG. 4. In this example, the initial polymeric hydrogel 14' is includes N-(5-azidoacetamidylpentyl) acrylamide as the first monomeric unit M1 and acrylamide as the second monomeric unit M2. When exposed to the fluid 24 including the positively chargeable moiety 26 (which, in this example, is propargyl choline bromide), the azide group of the first monomeric unit M1 and the alkyne group of the compound 30 undergo a copper-catalyzed azide-alkyne cycloaddition (CuAAC) reaction. The result of the CuAAC reaction is the cationic polymeric hydrogel 14, which includes the cationic moiety 16 (which, in this example, is a N,N,N-trimethylethanolammonium cation) attached to the triazole of the monomeric unit M1'.

In the example shown in FIG. 4, the fluid 24 may include water. A concentration of the compound 30 in the fluid 24 may range from about 100 nM to about 100 μM. Because the linking reaction is a CuAAC reaction, the fluid 24 may also include a catalyst and a ligand, or a catalyst, a ligand, and a reducing agent. These components may be added to the fluid 24 so that they are introduced to the flow cell 10$_P$. Any copper catalyst that generates copper (II) ions may be used, such as $CuSO_4$. Any ligand may be used, such as N,N,N', N",N"-pentamethyldiethylenetriamine (PMDTA). Any reducing agent may be used, such as sodium ascorbate. In one example, the fluid 24 includes from about 0.25 mol % to about 2 mol % of the copper catalyst and from about 5 mol % to about 10 mol % of the reducing agent.

In this example, the incubation temperature ranges from about 18° C. to about 60° C. and the incubation time ranges from about 30 minutes to about 12 hours. In another example, the incubation temperature for the CuAAC reaction ranges from about 18° C. to about 22° C., and the time ranges from about 60 minutes (1 hour) to about 6 hours or from about 6 hours to about 12 hours.

It is to be understood that the example reaction shown in FIG. 4 is one example of the attachment reaction, and that other monomeric units M1, M2, other linkers 28, and/or other positively chargeable moieties 26 may be used.

Figure 5A:
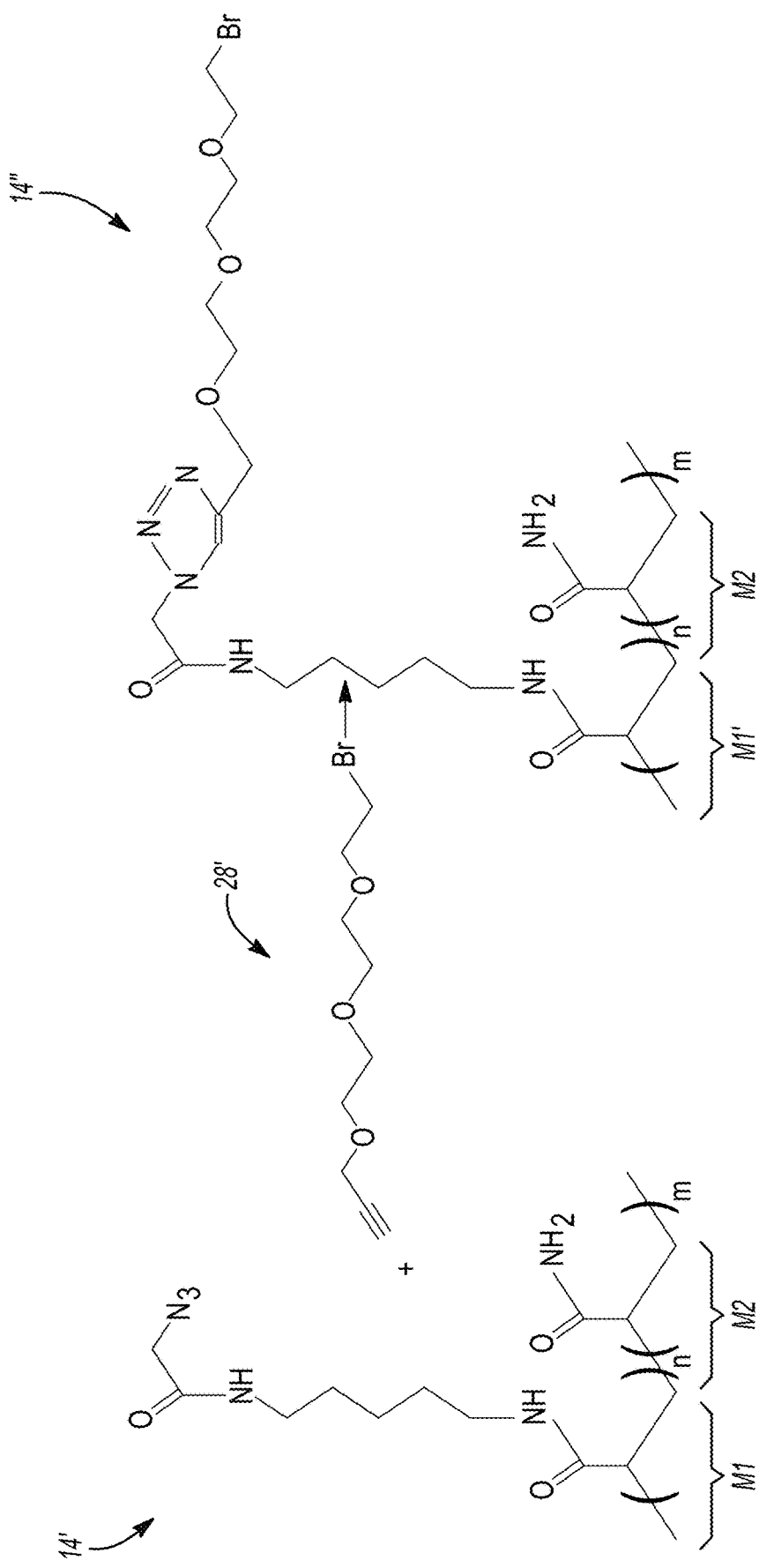
FIGS. 5A and 5B together depict a chemical formula illustrating the formation of still another example of a cationic polymeric hydrogel.

In still other examples, a combination of the methods shown in FIG. 3 and FIG. 4 may be used to generate the cationic polymeric hydrogel 14 including the cationic moiety 16. One example is shown in FIG. 5A and FIG. 5B.

In this example, a linker 28' including a terminal azide or alkyne at one end and a terminal negatively chargeable atom (e.g., bromine, iodine, or another weak nucleophile) at the other end is attached to the surface moiety of the monomeric unit M1 of the initial polymeric hydrogel 14'. When the linker 28' includes a terminal azide, the surface moiety of the monomeric unit M1 is an alkyne, and when the linker 28' includes a terminal alkyne, the surface moiety of the monomeric unit M1 is an azide. The linking reaction may be performed in a similar manner as described in reference to FIG. 4. This results in a modified polymeric hydrogel 14", as shown in FIG. 5A.

The modified polymeric hydrogel 14" may then be exposed to a displacement reaction as described in reference to FIG. 3. A fluid 24, including a positively chargeable moiety 26 that is stronger than the negatively chargeable atom (e.g., bromine) of the modified polymeric hydrogel 14", may be introduced to the flow cell 10$_P$. As described in reference to FIG. 3, the positively chargeable moiety 26 will displace and replace the negatively chargeable atom to form another example of the cationic polymeric hydrogel 14.

Figure 5B:
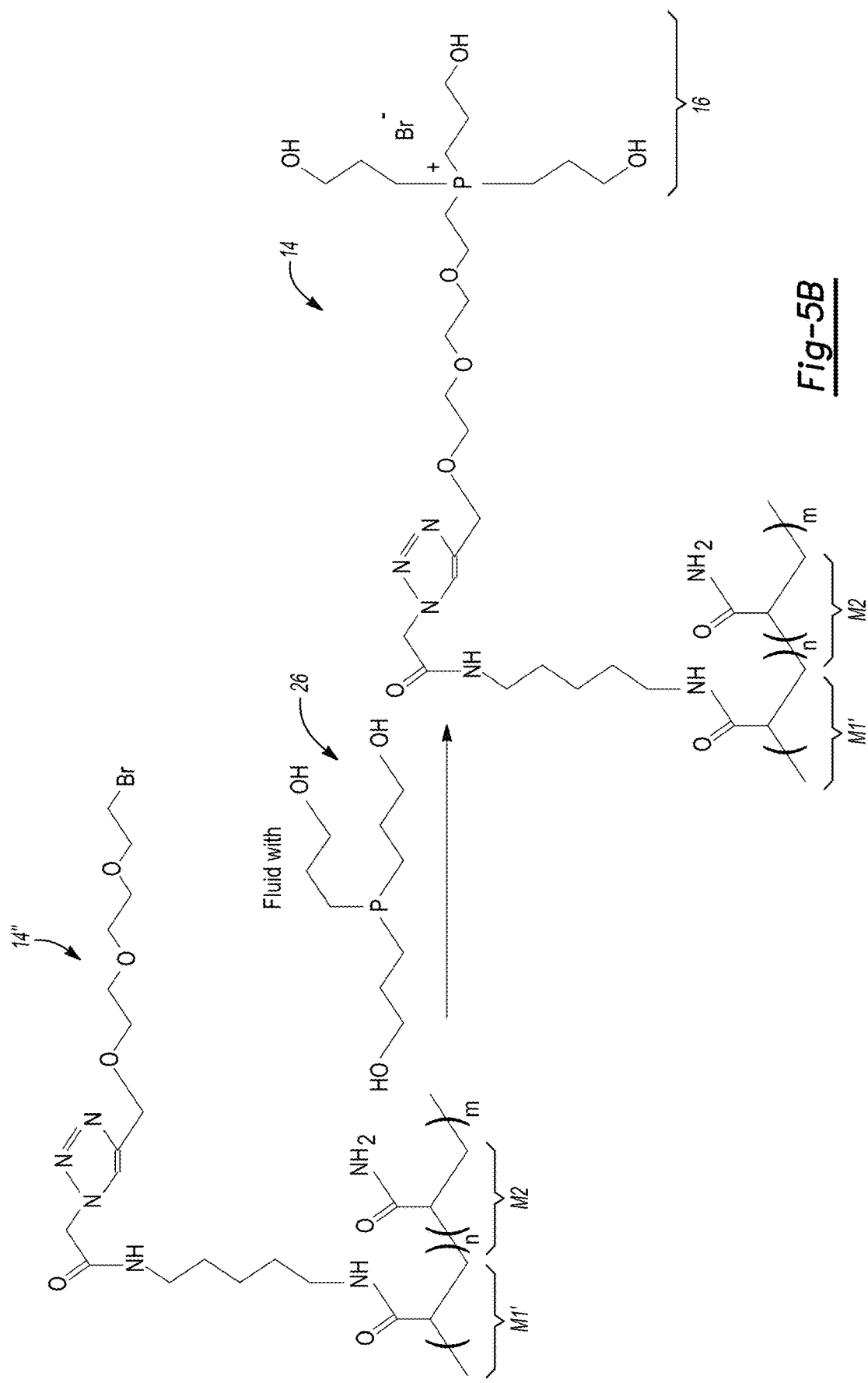

When incubation takes place at a temperature and for a suitable time, the cationic polymeric hydrogel 14 is formed (as shown in FIG. 5B), which includes both the cationic moiety 16 and the amplification primer(s) 18 at the surface thereof.

It is to be understood that the example reactions shown in FIG. 5A and FIG. 5B are one example of the displacement and attachment reactions, and that other monomeric units M1 (e.g., including another displaceable surface moiety), M2, other linkers 28, and/or other positively chargeable moieties 26 may be used.

The flow cell 10 with the positively charged (cationic) polymeric hydrogel 14 is shown in FIG. 2B. The flow cell 10 shown in FIG. 2B includes the substrate 12, the cationic polymeric hydrogel 14 on the substrate 12, the cationic moiety 16 i) integrated into a monomeric unit M1' of the cationic polymeric hydrogel 14 or ii) attached to the monomeric unit M1' of the polymeric hydrogel 14 through a linker 28, 28', and an amplification primer 18 attached to the cationic polymeric hydrogel 14.

The positively charged polymeric hydrogel 14 can attract a negatively charged complex or sample introduced to the flow cell 10, and thus an additional capture site may not be utilized.

Additional Flow Cell Architectures

While one example of the flow cell architecture is shown in FIG. 2B, it is to be understood that other flow cell architectures may be used.

Figure 6:
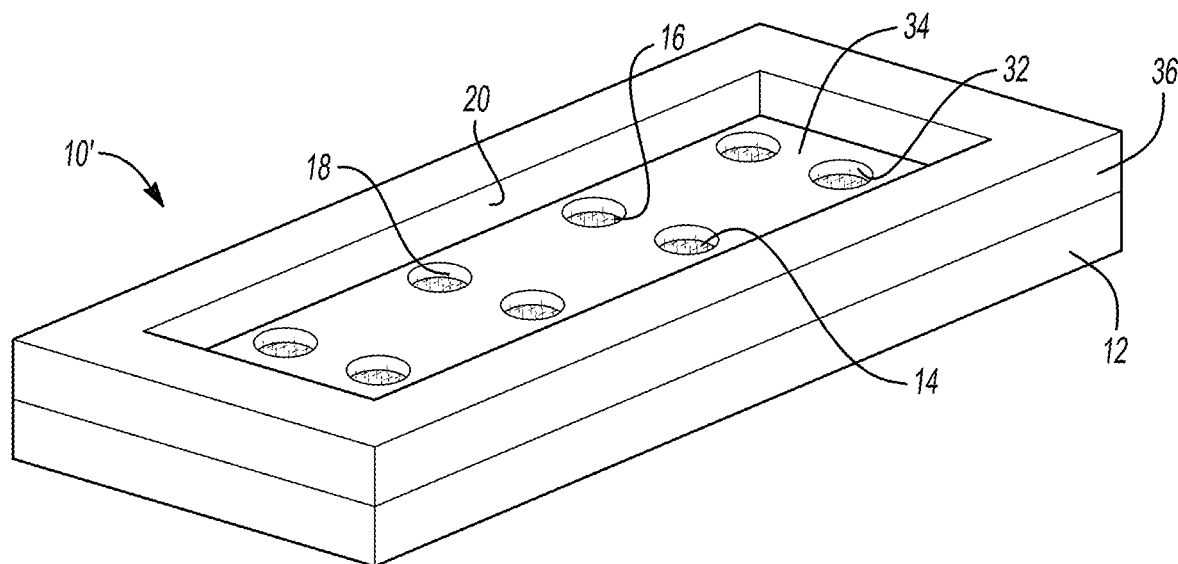
FIG. 6 is a semi-schematic, perspective view of a portion of another example of a flow cell disclosed herein.

Another example of the flow cell 10' is shown in FIG. 6. This example is similar to the example shown in FIG. 2B, except that the substrate 12 includes a plurality of depressions 32 separated by interstitial regions 34, and the cationic polymeric hydrogel 14 (including the cationic moiety 16) and the amplification primer(s) 18 are positioned within each of the depressions 32. In the example shown in FIG. 6, the depressions 32 are defined in the lane 20.

In this example, the depressions 32 may be patterned into the substrate 12. Patterning may involve etching the depressions 32 into the substrate 12 and/or using imprint lithography. The depressions 32 may then be functionalized with the cationic polymeric hydrogel 14 (including the cationic moiety 16) and the amplification primer(s) 18 as described herein. Interstitial regions 34 between the depressions 32 do not have the cationic polymeric hydrogel 14 (including the cationic moiety 16) or the amplification primer(s) 18 thereon. This may be due to the initial polymeric hydrogel 14' being polished from the interstitial regions 34. After the depressions 32 are functionalized, an additional material 36 (e.g., a hydrophobic material) may be attached (e.g., bonded, adhered, etc.) to the substrate 12 (e.g., at the perimeter) to define the walls of the lane 20 around the depressions 32.

The depressions 32 may be distributed across the flow cell 10' in any suitable pattern or layout. When the flow cell 10' includes multiple lanes 20, the pattern of depressions 32 may be the same, or different patterns of depressions 32 may be used in different lanes 20. Many different patterns/layouts of the depressions 32 may be envisaged, including regular, repeating, and non-regular patterns. In an example, the depressions 32 are disposed in a hexagonal grid for close packing and improved density. Other layouts may include, for example, parallelogram layouts (i.e., rectangular, square, etc.), triangular layouts, circular layouts, and so forth.

Each depression 32 may have any suitable shape (and corresponding 3-dimensional geometry), such as a circle (as shown in FIG. 6), an oval, a polygon (e.g., triangle, quadrilateral, pentagon, etc.), etc.

The size of each depression 32 may be characterized by its opening area, diameter, and/or length and width.

The area occupied by each depression opening can be selected so that a complex cannot enter the depression 32. In an example, the area for each depression opening can be at least can be at least about $1 \times 10^{-4}$ μm$^2$, at least $1 \times 10^{-3}$ μm$^t$, at least about $1 \times 10^{-2}$ μm$^2$, at least about 0.1 μm$^2$, at least about 0.5 μm$^2$, at least about 1 μm$^2$, or at least about 4 μm$^2$. The area occupied by each depression opening can be less than or between the values specified above.

In some instances, the diameter or length and width of each depression 32 can be at least can be at least about 1 nm, at least about 50 nm, at least about 100 nm, at least about 500 nm, or more, as long as the dimension is less than the lane diameter or length and width. An example of the depression diameter ranges from about 1 nm to about 500 nm. Another example of the depression diameter ranges from about 300 nm to about 2 μm.

The depressions 32 may also have a depth. As examples, the depth of each depression 32 can be at least about 10 nm, at least about 50 nm, at least about 1 μm, up to about 2 μm. It is to be understood that the depth of each depression 32 can be greater than, less than or between the values specified above.

In an example, the aspect ratio (diameter:depth) of the depressions 32 may range from about 1:1 to about 1:2, or from about 1:1.25 to about 1:1.75.

In this example, adjacent depressions 32 may be separated by the interstitial regions 34 within a given lane 20. The average depression pitch represents the spacing from the center of one depression 32 to the center of an adjacent depression 32 (center-to-center spacing) or from the right edge of one depression 32 to the left edge of an adjacent depression 32 (edge-to-edge spacing). The layout or pattern of the depressions 32 can be regular, such that the coefficient of variation around the average pitch is small, or the layout or pattern can be non-regular in which case the coefficient of variation can be relatively large. In either case, the average pitch can be, for example, at least about 10 nm, at least about 0.1 μm, at least about 0.5 μm, or more, depending upon the dimensions of the lane 20. Alternatively or additionally, the average pitch can be, for example, at most about 0.5 μm, at most about 0.1 μm, or less. The average pitch for a particular pattern of depressions 32 can be between one of the lower values and one of the upper values selected from the ranges above.

Figure 7:
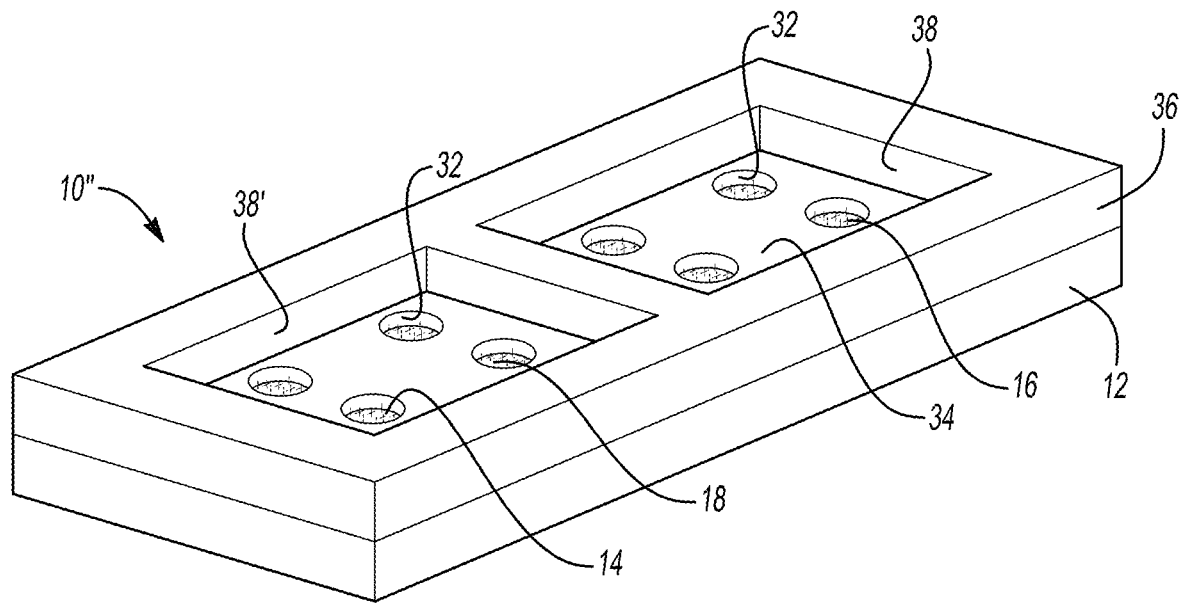
FIG. 7 is a semi-schematic, perspective view of a portion of still another example of a flow cell disclosed herein.

Another example of the flow cell 10" is shown in FIG. 7. This example is similar to the example shown in FIG. 6, except that the substrate 12 further includes a plurality of chambers 38, 38', and wherein a sub-set of the plurality of depressions 32 are located within a perimeter of each of the plurality of chambers 38, 38'. Similar to FIG. 6, the cationic polymeric hydrogel 14 (including the cationic moiety 16) and the amplification primer(s) 18 are positioned within each of the depressions 32.

In this example, the depressions 32 may be patterned into the substrate 12. Patterning may involve etching the depressions 32 into the substrate 12 and/or using imprint lithography. The depressions 32 may then be functionalized with the cationic polymeric hydrogel 14 (including the cationic moiety 16) and the amplification primer(s) 18 as described herein. Interstitial regions 34 between the depressions 32 do not have the cationic polymeric hydrogel 14 (including the cationic moiety 16) or the amplification primer(s) 18 thereon. After the depressions 32 are functionalized, an additional material 36 (e.g., a hydrophobic material) may be attached (e.g., bonded, adhered, etc.) to the substrate 12 (e.g., at the perimeter) to define walls of the chambers 38, 38' around the sub-sets of depressions 32.

The chambers 38, 38' may be distributed across the substrate 12 in any suitable pattern or layout. Many different layouts of the chambers 38, 38' may be envisaged, including regular, repeating, and non-regular patterns. In an example, the chambers 38, 38' are disposed in a hexagonal grid for close packing and improved density. Other layouts may include, for example, parallelogram layouts (i.e., rectangular, square, etc.), triangular layouts, circular layouts, and so forth. In some examples, the layout or pattern can be an x-y format of the chambers 38, 38' that are in rows and columns.

The chambers 38, 38' may have any suitable shape, such as a square, a circle, an oval, a polygon (e.g., triangle, quadrilateral, pentagon, etc.), etc.

The size of each chamber 38, 38' may be characterized by its opening area, diameter, and/or length and width. As shown in FIG. 7, the flow cell 10" has a plurality of depressions 32 located within each of the chambers 38, 38'. As such, the size of the chamber 38, 38' is larger than the size of each depression 32. In other words, the dimension(s) of the chamber 38, 38' is/are larger than the dimension(s) of each depression 32. In this example, "dimension" refers to the area occupied by each chamber opening or depression opening, and/or the diameter of the chamber 38, 38' or depression 32, and/or the length and width of each chamber 38, 38' or depression 32. In the example shown in FIG. 7, the opening area and the diameter of each of the chambers 38, 38' is larger than the opening area and the diameter of each of the depressions 32. The opening area, and the diameter or length and width of each chamber 38, 38' depends upon the number of depressions 32 that are to be located within the chamber 38, 38'.

Figure 8A:
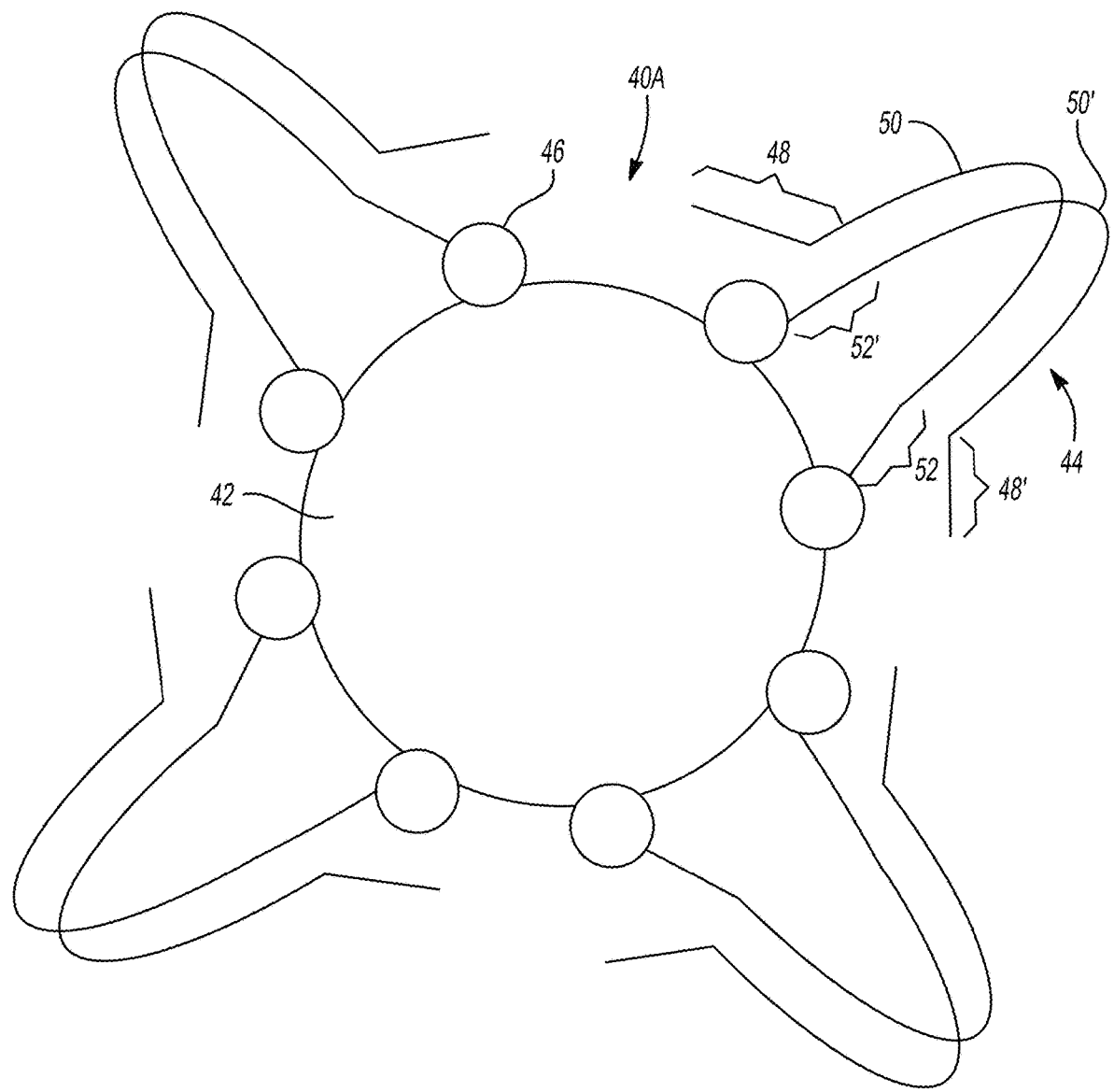
FIGS. 8A through 8C are schematic illustrations of different examples of the complexes disclosed herein.
Figure 8B:
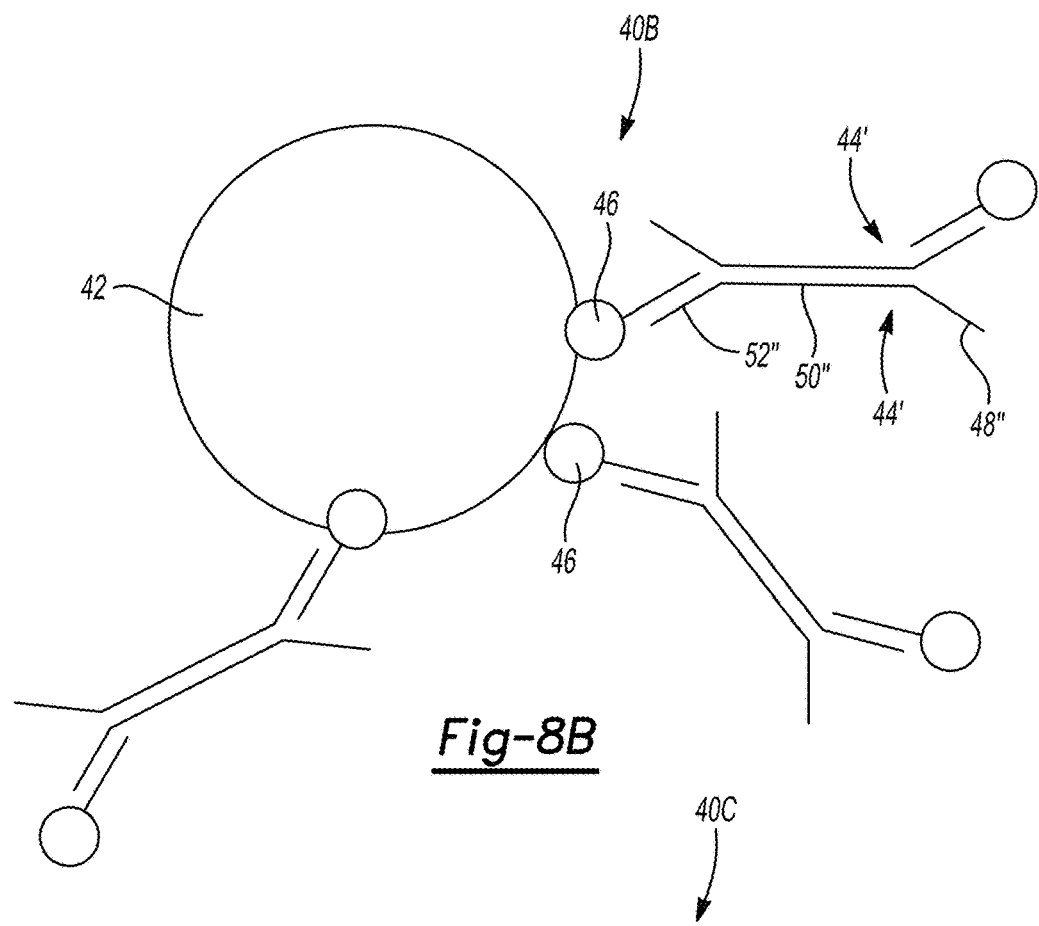
Figure 8C:
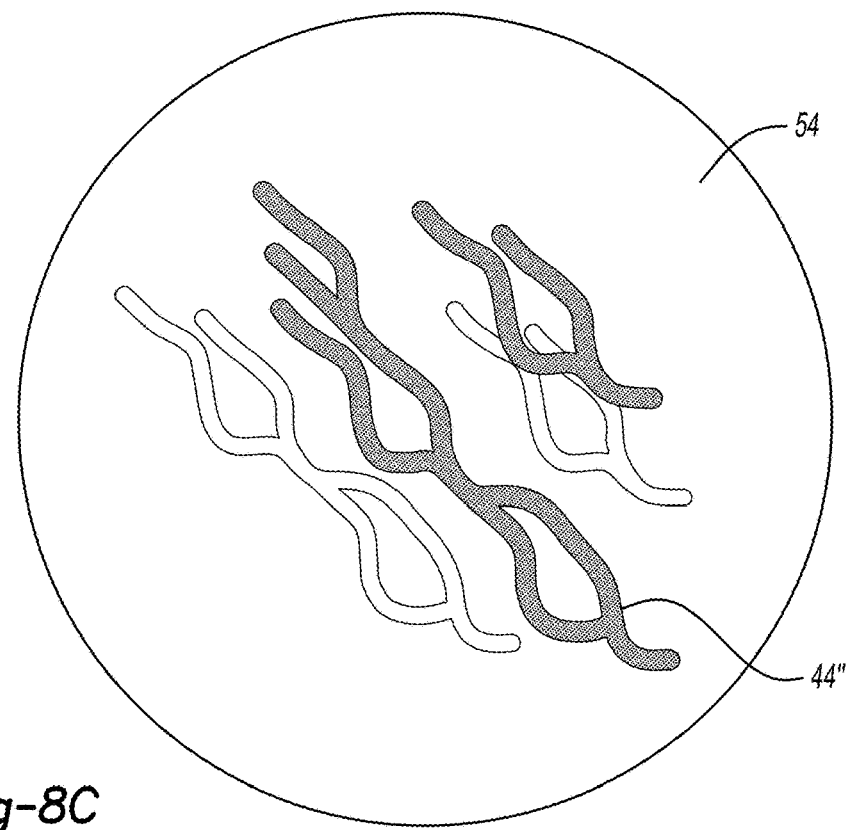

The area occupied by each chamber opening can be selected so that a complex (examples of which are shown in FIG. 8A through FIG. 8C) can enter the chamber 38, 38'. In an example, the area for each chamber opening can be at least about 1 µm², at least about 10 µm², at least about 100 µm², or more. The area occupied by each chamber opening can be greater than or between the values specified above.

In some instances, the diameter or length and width of each chamber 38, 38' can be at least about 1 µm, at least about 10 µm, at least about 20 µm, at least about 30 µm, at least about 40 µm, at least about 50 µm, at least about 100 µm, or more. An example of the chamber diameter ranges from about 1 µm to about 1000 µm. Another example of the chamber diameter ranges from about 10 µm to about 50 µm. When the chamber 38, 38' has a length and width, it is to be understood that the length and width may be the same or different.

The chamber 38, 38' may also have a depth that depends upon the technique used to form the chamber 38, 38'. For example, the depth of each chamber 38, 38' can be a monolayer thick when microcontact, aerosol, or inkjet printing is used to deposit the additional material 36 that defines the chambers 38, 38'. For other examples, the depth of each chamber 38, 38' can be about 1 µm, about 10 µm, about 50 µm, or more. In another example, the depth is at least about 50% of an average diameter of a complex that is to be introduced into the chamber 38, 38'. In an example, this depth may range from about 10 µm to about 30 µm. In addition to the positively charged polymeric hydrogel 14 that attracts the released library fragments, the depth of the chambers 38, 38' can help block lateral diffusion of released library fragments between adjacent chambers 38, 38'. As such, the released library fragments may be maintained within the chamber 38, 38' without any external immobilization agent. In another example, the depth is about 5 µm or less. It is to be understood that the depth of each chamber 38, 38' can be greater than, less than or between the values specified above.

Adjacent chambers 38, 38' may be separated by the surface of the additional material 36. The average chamber pitch represents the spacing from the center of one chamber 38, 38' to the center of an adjacent chamber 38, 38' (center-to-center spacing) or from the right edge of one chamber 38, 38' to the left edge of an adjacent chamber 38, 38' (edge-to-edge spacing). The layout or pattern of the chambers 38, 38' can be regular, such that the coefficient of variation around the average pitch is small, or the layout or pattern can be non-regular in which case the coefficient of variation can be relatively large. In either case, the average pitch can be, for example, at least about 1 µm, at least about 5 µm, at least about 10 µm, at least about 100 µm, or more. In one example, the average pitch is 2 times the diameter of the chamber 14. The average pitch for a particular pattern of chambers 38, 38' can be between one of the lower values and one of the upper values selected from the ranges above. While example average chamber pitch values have been provided, it is to be understood that other average chamber pitch values may be used.

Each sub-set of depressions 32 is location within a perimeter of each of the plurality of chambers 38, 38'.

While not shown in FIG. 6 or FIG. 7, the lane 20 of the flow cell 10' or each chamber 38, 38' of the flow cell 10" may include a capture site that can attract a complex or sample introduced to the flow cell 10' or 10". More specifically, at least a portion of the interstitial region 34 within the lane 20 or chamber 38, 38' may include a capture site.

The capture site(s) may be physically and/or chemically capable of immobilizing a complex or sample on the substrate 12 (e.g., on the interstitial regions 34) in the lane 20 or in the chambers 38, 38'.

The capture site(s) may be positioned at any suitable location. The position of the capture site(s) across the substrate 12 may be uniform or may be non-uniform. The capture sites may have any suitable shape, geometry and dimensions, which may depend, at least in part, on the configuration of the capture sites (e.g., a patch, a well, a protrusion, etc.), and the type of complex or sample that is to be captured by the capture site(s).

In some examples, the capture site(s) is a chemical capture agent that is applied on a portion of the interstitial region 34. Any examples of the chemical capture agent disclosed herein may be used. In one example, the respective chemical capture agents may be deposited in the desirable locations using microcontact printing, or another suitable technique.

In other examples, the capture site(s) include a well that is defined in the surface of the substrate 12. The well may be formed using etching or imprinting depending upon the substrate 12 that is used. The well may have any suitable shape and geometry, such as those set forth herein for the depressions 32. In some examples, the well does not have an additional chemical capture agent added thereto. In these examples, the opening dimensions enable the complex or sample to self-assemble into the corresponding well (e.g., based on shape). In other examples, the well does have a chemical capture agent added thereto.

Other examples of the capture sites include the well and a capture bead having a chemical capture agent on a surface thereof. The capture bead may be sized to fit into the wells. In some examples, the capture beads may be co-planar with or extend slightly above the adjacent interstitial regions 34 so that the complex or sample that ultimately attaches thereto is not confined within the well. In an example, the capture bead is selected from the group consisting of silicon dioxide, a superparamagnetic material, polystyrene, and an acrylate. Any examples of the chemical capture agent disclosed herein may be used on the surface of the capture bead, and may be coated on the capture bead before it is introduced into the well.

The depth of a capture site well may vary depending upon whether the chemical capture agent is to be introduced thereto and whether the capture bead is to be introduced thereto. The depth may be selected at least to accommodate these materials (i.e., the material is contained within the wells). In an example, the depth of the well ranges from about 1 nm to about 5 microns.

As another example, the capture sites include protrusions that are defined in the substrate 12. The protrusions are three-dimensional structures that extend outward (upward) from an adjacent surface. The protrusions may be generated via etching, photolithography, imprinting, etc. While any suitable three-dimensional geometry may be used for the protrusion capture sites, a geometry with an at least substantially flat top surface may be desirable. Example protrusion geometries include a sphere, a cylinder, a cube, polygonal prisms (e.g., rectangular prisms, hexagonal prisms, etc.), or the like.

Different chemical capture agents may be applied on the top surface of the respective protrusion capture sites. Any examples of the chemical capture agent disclosed herein may be used, and any deposition technique may be used to apply the chemical capture agent to the top surface of the protrusions.

It is to be understood that any combination of the types of capture sites may be used together (e.g., capture agent and well) on the flow cell 10', 10".

The flow cell 10 is shown with the lid 21 bonded to the substrate 12 while the flow cells 10', 10" are shown without the lid 21 bonded to the substrate 12. It is to be understood that some examples of the flow cells 10, 10', 10" may have the lid 21 bonded to at least a portion of the substrate 12, e.g., at the surface 22. The lid 21 may be positioned on the surface 22 so that it defines a single flow lane 20 or multiple, fluidically separated flow lanes 20, or multiple chambers 38, 38' which may or may not be fluidically separated.

The lid 21 may be any material that is transparent to an excitation light that is directed toward the substrate 12. As examples, the lid 21 may be glass (e.g., borosilicate, fused silica, etc.), plastic, or the like. A commercially available example of a suitable borosilicate glass is D 263®, available from Schott North America, Inc. Commercially available examples of suitable plastic materials, namely cyclo olefin polymers, are the ZEONOR® products available from Zeon Chemicals L.P.

The lid 21 may be bonded to the substrate surface 22 using any suitable technique, such as laser bonding, diffusion bonding, anodic bonding, eutectic bonding, plasma activation bonding, glass frit bonding, or others methods known in the art. In an example, a spacer layer 23 may be used to bond the lid 21 to the substrate surface 22. The spacer layer 23 may be any material that will seal at least some of the substrate 12 and the lid 21 together.

In other examples, the flow cells 10, 10', 10" do not include a lid, but rather include two substrates 12 bonded together. In these examples, the reactive surfaces (e.g., the polymeric hydrogel 14, the primers 18) of the substrates 12 face each other. The substrates 12 may be bonded together using similar techniques and materials described for the lid 21 and the substrate 12.

Kits

The flow cell $10_P$ may be part of a kit that may be used to introduce the positive charges to the initial polymeric hydrogel 14'. In an example, the kit includes i) the flow cell $10_P$, which includes a substrate 12, an initial polymeric hydrogel 14' positioned on the substrate 12 and having a surface moiety selected from the group consisting of a negatively chargeable atom, an azide group, and an alkyne group, and an amplification primer 18 attached to the initial polymeric hydrogel 14'; and ii) a fluid 24 including a positively chargeable moiety 26 that is to interact or react with the surface moiety to form a cationic polymeric hydrogel 14 including a cationic moiety 16.

Any examples of the flow cell architectures disclosed herein, including those for flow cells 10, 10', 10", may be used in the flow cell $10_P$ in the kit. Moreover, any example of the substrate 12, the initial polymeric hydrogel 14', and the amplification primer 18 may be used. Still further, any example of the fluid 24 including the positively chargeable moiety 26 may be used in the kit.

The kit may be used to perform the method 100 as described herein.

Complexes for Use with the Flow Cells

Examples of the flow cell 10, 10', 10" may be particularly suitable for use with examples of the complexes disclosed herein. A complex includes a carrier (e.g., a hydrogel support or a solid support) and sequencing-ready nucleic acid fragments attached to or contained within the carrier. Examples of suitable complexes are shown in FIG. 8A through FIG. 8C. While some example methods for making the complexes are described, it is to be understood that other methods may be used as long as sequencing-ready nucleic acid fragments attached to or contained within the carrier.

FIG. 8A illustrates a complex 40A that includes a solid support 42 and sequencing-ready nucleic acid fragments 44 attached to the solid support 42.

In one example, to form this complex 40A, an adapter sequence 52, 52' is bound to the solid support 42 through one member 46 of a binding pair. In an example, this adapter sequence 52, 52' includes a first sequencing primer sequence (e.g., a read 1 sequencing primer sequence) and a first sequence (e.g., a uracil-modified P5 sequence) that is complementary to at least a portion of one of the amplification primers 18 (e.g., P5) on the flow cell 10, 10', 10". This adapter sequence 52, 52' is bound to the one member 46 of the binding pair (e.g., biotin) so that it can be bound to the surface of the solid support 42 (which includes the other member (e.g., avidin, streptavidin, etc.) of the binding pair. This adapter sequence may also include an index sequence.

A Y-adapter may be mixed with a transposase enzyme (e.g., two Tn5 molecules) to form a transposome. The Y-adapter may include two mosaic end sequences that are hybridized to each other. One of the mosaic end sequences may be attached to another adapter 48, 48', which includes a second sequencing primer sequence (e.g., a read 2 sequencing primer sequence), a second sequence (e.g., a uracil-modified P7 sequence) that is complementary to at least a portion of another one of the amplification primers 18 (e.g., P7) on the flow cell 10, 10', 10", and optionally an index/barcode sequence.

A tagmentation process may then be performed. A fluid (e.g., a tagmentation buffer) including a sample (e.g., DNA) may be added to the transposomes and to the solid support 42 having the adapter sequence 52, 52' bound thereto. As the sample contacts the transposomes, the DNA is tagmented (fragmented and tagged with the adapter 52, 52' on the solid support 42), and is bound to the Y-adapter (e.g., through ligation of the free mosaic end sequence). Successive tagmentation of the sample results in a plurality of bridged molecules between transposomes. The bridged molecules wrap around the solid support 42. The transposomes maintain the contiguity of the bridged molecules. To complete the sequencing ready fragments 44, further extension and ligation is undertaken to ensure sample fragments 50, 50' are attached to sequences 48 and 48'.

The transposase enzyme may then be removed via sodium dodecyl sulfate (SDS) treatment or heat or proteinase K digestion. Removal of the transposase enzymes leaves the sequencing-ready nucleic acid fragments 44 attached to the solid support 42.

The resulting complex 40A is shown in FIG. 8A. The bridged molecules are the sequencing-ready nucleic acid fragments 42, each of which includes a fragment 50, 50' and adapter sequences 48 and 52 or 48' and 50' attached at either end. The adapter sequences 52, 52' are those initially bound to the solids support 42, and include the first sequencing primer sequence and the first sequence complementary to the flow cell primer. The adapter sequences 52, 52' are attached to the one member 46 of a binding complex/pair. The adapter sequences 48, 48' are from the Y-adapter, and include the second sequence complementary to another flow cell primer and the second sequencing primer sequence. Because each sequencing-ready nucleic acid fragment 44 includes suitable adapters for amplification (e.g., bridge amplification) and sequencing, PCR amplification is not performed. These fragments 44 are thus sequencing-ready. Moreover, because the library fragments 44 are from the same sample, the fragments 44 may be suitable for linked long read applications.

FIG. 8B illustrates another complex 40B that includes a solid support 42 and sequencing-ready nucleic acid fragments 44' attached to the solid support 42. In one example, a PCR-free nucleotide library is created in a tube, and then the library is hybridized to the solid support 42 in the tube. In the example shown in FIG. 8B, primers (e.g., adapters 52", 48") having one member 46 of a binding pair are added to the library fragments 50" in the tube, and then the sequencing-ready nucleic acid fragments 44' are bound to the solid support 42. In another example, the solid support 42 may have primers attached thereto via a binding pair (e.g., avidin on the support 42 and biotin attached to the primer). These primers hybridize to adapters 52" attached to the library fragments 50" (and thus the primer and binding pair member are at one end of the fragments and not at the other). In another example, extension may be performed using a strand displacing enzyme. This will result in an entirely double stranded library (e.g., no fork or Y-adapter, as shown in FIG. 8B). The sequencing-ready nucleic acid fragments 44' may be released on the flow cell via denaturation.

FIG. 8C illustrates an example of the complex 40C that includes a hydrogel support 54 and sequencing-ready nucleic acid fragments 44" contained within the hydrogel support 54.

To form this complex 40C, a fluid containing hydrogel monomer(s) and/or polymer(s) and crosslinker(s) are mixed in the presence of the sample (e.g., genetic material). This fluid may be loaded into mineral oil or another suitable hydrophobic fluid, and emulsified to generate droplets. A radical initiator may be added to polymerize and/or crosslink the hydrogel monomer(s) and/or polymer(s) and form the hydrogel support 54.

When forming the complex 40C, the fluid may be water; the monomer may be selected from the group consisting of acrylamide, N,N'-bis(acryloyl)cystamine, bisacrylamide, diacrylate, diallylamine, triallylamine, divinyl sulfone, ethyleneglycol diallyl ether, ethyleneglycol diacryate, trimethylolpropane trimethacrylate, ethoxylated trimethylol diacrylate, ethoxylated pentaerythritol tetracrylate, a collagen monomer, and combinations thereof; and/or the polymer may be selected from the group consisting of polyethylene glycol-thiol, polyethylene glycol-acrylate, polyethylene glycol diacrylate, polyethylene glycol (e.g., having a weight average molecular weight ranging from about 100 to about 200,000), polypropylene oxide, polyacrylic acid, poly(hydroxyethyl methacrylate), poly(methyl methacrylate), poly(N-isopropylacrylamide), poly(lactic acid), poly(lactic-co-glycolic acid), polycaprolactone, poly(vinylsulfonic acid), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, a collagen polymer, and combinations thereof. The crosslinker forms bonds, e.g., disulfide bonds, in the polymer of the hydrogel support 54. The crosslinker may be reversible, in that it can be crosslinked and uncrosslinked depending on the chemical to which it is exposed. In example, the reversible crosslinker is a bisacrylamide crosslinker containing disulfide bonds, which can be broken down with reducing agents, such as dithiothreitol (DTT), tris-(2-carboxyethyl)phosphine (TCEP), or tris-(3-hydroxypropyl)phosphine (THP). In an example, the crosslinker is selected from the group consisting of acrylamide, N,N'-bis (acryloyl)cystamine, bisacrylamide, 1,4-diacroylpiperazine, N—N'-diallyl L-tartardiamide, and N—N'-(1,2-dihydroxyethylene)-bis-acrylamide. In an example, the radical initiator may be a photoinitiator. Examples of photoinitiators include azobisisobutyronitrile, benzoyl peroxide, eosin-5-isothiocyanate. This type of radical initiator may be used because it will not initiate crosslinking until exposed to light of an appropriate wavelength. In another example, the radical initiator may initiate crosslinking when exposed to a radical source. An example of this type of radical initiator is tetramethylethylenediamine (TEMED).

The sample becomes encapsulated within the hydrogel support 54 because its size is sufficient that it cannot pass through the pores of the hydrogel support 54. In some examples, the sample is DNA or RNA and is at least about 100 nucleotides in length (e.g., 1,000 nucleotides or more, 10,000 nucleotides or more, 500,000 nucleotides or more, etc.). In some examples, the pore size of the hydrogel support 54 refers to an average diameter or an average effective diameter of a cross-section of the pores, based on a measurement of a plurality of pores. The effective diameter of a cross-section that is not circular equals the diameter of a circular cross-section that has the same cross-sectional area as that of the non-circular cross-section. In an example, the pore size ranges from about 10 nm to about 100 nm.

Library preparation can then take place within the hydrogel support 54. Multiple reagent exchange may take place through the pores of the hydrogel support 54. The sample and any library fragments generated therefrom are maintained within the hydrogel matrix. Library preparation may involve fragmenting the sample and adding adapters that will result in sequence-ready fragments 44".

In an example, library preparation may be performed via tagmentation that takes place within the hydrogel support 54. The resulting complex 40C is shown in FIG. 8C. The adapter sequences include suitable adapters for amplification and sequencing and thus the resulting fragments 44" are sequencing-ready. In another example, library preparation may be performed using polymerase extension, which results in a double stranded library. This example library needs to be denatured prior to release form the hydrogel support 54 and seeding.

Methods Involving Complexes

Some examples of the method disclosed herein utilize an example of the flow cell 10, 10', 10" disclosed herein and any one of the complexes 40A, 40B, or 40C. As described above, each of the complexes 40A, 40B, or 40C includes sequence-ready fragments obtained from the same sample of genetic material. When one or a few of the complexes are isolated within the lane 20 or chambers 38, 38', spatial co-localization of the libraries from the same sample is achieved.

In an example method, the complexes 40A, 40B, or 40C are introduced into the flow cell 10, 10', 10", for example through one or more input ports 25. The complexes 40A, 40B, or 40C may be introduced into a fluid, such as such as Tris-HCl buffer or 0.5× saline sodium citrate (SSC) buffer. At least some complexes 40A, 40B, or 40C from the fluid will settle into at least some of the lane(s) 20 and/or chambers 38, 38'. When the flow cell 10 is used, the negatively charged sequencing ready fragments 44, 44', 44' of the complexes 40A, 40B, or 40C may be attracted to the positively charged polymeric hydrogel 14 in the lane 20. When the flow cell 10' or 10" is used, the positively charged polymeric hydrogel 14 is confined with in the depressions 32. In some of these examples, the complexes 40A, 40B, or 40C may settle and remain in the lane 20 or chambers 38, 38', in part due to the depth of the lane 20 or chambers 38, 38'. In some other of these examples, the lane 20 or chambers 38, 38' may include a capture site that the complexes 40A, 40B, or 40C adhere to.

It is to be understood that some complexes 40A, 40B, or 40C may not settle, and these complexes 40A, 40B, or 40C will be removed from the flow cell 10, 10', 10" before further processes. It is also to be understood that some lanes 20 or chambers 38, 38' may receive one or more of the complexes 40A, 40B, or 40C, while others of the lanes 20 or chambers 38, 38' may receive no complexes 40A, 40B, or 40C. The complex 40A, 40B, or 40C distribution may be random when capture sites are not included, or may be more controlled when capture sites are included.

This example method then includes washing away non-trapped complexes 40A, 40B, or 40C from the flow cell 10, 10', 10". Washing may involve introducing the fluid into the flow cell 10, 10', 10". The flow may push any complexes 40A, 40B, or 40C that have not settled out through an exit port 27 of the flow cell 10, 10', 10".

This example of the method then includes causing the carrier (e.g., the solid support 42 or the hydrogel support 54) of the trapped complexes 40A, 40B, or 40C to release the sequencing-ready nucleic acid fragments 44, 44', or 44" into the respective lane 20 or chamber 38, 38' in which each complex 40A, 40B, or 40C is trapped.

Causing the carrier (i.e., support 42 or 54) to release the sequencing-ready nucleic acid fragments 44, 44', or 44" may vary, depending upon the complex 40A, 40B, or 40C that is used. In one example, the carrier is the solid support 42, and the causing involves introducing a cleaving agent to the flow cell 10, 10', 10". The cleaving agent may initiate chemical, enzymatic, or photo-chemical release of the sequencing-ready nucleic acid fragments 44, 44' from the solid support 42. In these examples, another stimulus, such as heat or light, may trigger the cleaving agent to release the library fragments 44 or 44' from the solid support 42. As one example, free biotin may be introduced as the cleaving agent, and heating to about 92° C. may be used to induce biotin-oligo release from the solid support 42.

In other examples, the complex 40C is used and thus the carrier is the hydrogel support 54. In these other examples, causing library release may involve heating the flow cell 10, 10', 10", introducing a cleaving agent to the flow cell 10, 10', 10", or combinations thereof. Heating to release the library fragments 44" from the hydrogel support 54 may involve heating to a temperature of about 90° C. The entire flow cell 10, 10', 10" may be heated, and when the complexes 40C heat up, the hydrogel support 54 may degrade to release the fragments 44". In some examples, the cleaving agent may include one or more components that can depolymerize the hydrogel support 54 and release the sequencing-ready fragments 44" therefrom. As examples, the cleaving agent includes dithiothreitol (DTT), tris-(2-carboxyethyl)phosphine (TCEP), or tris-(3-hydroxypropyl)phosphine (THP). In other examples, the cleaving agent is light. In these examples, the crosslinker used to form the hydrogel support 54 may include a photo-cleavable moiety, and exposure of the complexes 40C to light of an appropriate wavelength can cleave this moiety and degrade the hydrogel support 54.

Transport and seeding of the sequencing-ready nucleic acid fragments 44, 44', or 44" are controlled, in part, by the positive charges of the cationic polymeric hydrogel 14. The sequencing-ready nucleic acid fragments 44, 44', 44" are negatively charged, and thus are attracted to the positively charged polymeric hydrogel 14. As such, the fragments 44, 44', or 44" of any particular complex 40A, 40B, or 40C will be confined to the lane 20 or chamber 38, 38' to which the particular complex 40A, 40B, or 40C is confined.

In addition to the attractive force of the cationic polymeric hydrogel 14, the depth of the lane 20 or chambers 38, 38' may also restrict transport and seeding of the sequencing-ready nucleic acid fragments 44, 44', or 44", and thus an external immobilizing agent may not introduced to the flow cell 10, 10', 10".

With the flow cells 10, 10', 10" disclosed herein, the cationic polymeric hydrogel 14 can attract the sequencing-ready nucleic acid fragments 44, 44', or 44" immediately after their release, which enables the amplification primers 18 to seed the released sequencing-ready nucleic acid fragments 44, 44', or 44" in a relatively confined manner. In an example, seeding is accomplished through hybridization between the first or second sequence of the fragment 44, 44', or 44" and a complementary one of the primers 18. Seeding may be performed at a suitable hybridization temperature for the fragment 44, 44', or 44" and the primer(s) 18.

The seeded sequencing libraries can then be amplified using any suitable method, such as cluster generation.

In one example of cluster generation, the sequencing-ready nucleic acid fragments 44, 44', or 44" are copied from the hybridized primers 18 by 3' extension using a high-fidelity DNA polymerase. The original sequencing-ready nucleic acid fragments 44, 44', or 44" are denatured, leaving the copies immobilized within the lanes 20 or depressions 32. Isothermal bridge amplification may be used to amplify the immobilized copies. For example, the copied templates loop over to hybridize to an adjacent, complementary primer 18, and a polymerase copies the copied templates to form double stranded bridges, which are denatured to form two single stranded strands. These two strands loop over and hybridize to adjacent, complementary primers 18 and are extended again to form two new double stranded loops. The process is repeated on each template copy by cycles of isothermal denaturation and amplification to create dense clonal clusters. Each cluster of double stranded bridges is denatured. In an example, the reverse strand is removed by specific base cleavage, leaving forward template polynucleotide strands. It is to be understood that clustering results in the formation of several template sequencing-ready nucleic acid fragments in each lane 20 or depression 32.

After cluster generation, the cationic moiety 16 may be cleaved from the cationic polymeric hydrogel 14. As such, the charge of the flow cell surface may be considered to be reversible. Cleavage of the cationic moiety 16 may be performed when the cationic moiety 16 is cleavable or is attached via a cleavable linker 28, 28' (e.g., includes a cleavable disulfide bond, or a photocleavable bond, or a cleavable nucleotide bond). Cleavage of the cationic moiety 16 may be accomplished by photocleaving, by exposure to acidic conditions (e.g., if the linker is acid labile), or by enzymatic cleavage (e.g., if a bi-functional DNA oligo is used as the linker 28, 28' to attach the cationic moiety 16). Cleavage of the cationic moiety 16 can reverse the charge of the flow cell surface, in part because the template sequencing-ready nucleic acid fragments attached to the polymeric hydrogel 14 are negatively charged.

After cluster generation (and in some instances after cleavage of the cationic moiety 16), sequencing may be performed. Any example of the flow cell 10, 10', 10'' disclosed herein may be used in a variety of sequencing approaches or technologies, including techniques often referred to as sequencing-by-synthesis (SBS), cyclic-array sequencing, sequencing-by-ligation, pyrosequencing, and so forth.

As one example, a sequencing by synthesis (SBS) reaction may be run on a system such as the HISEQ™, HISEQX™, MISEQ™, MISEQDX™, MINISEQ™, NOVASEQ™, NEXTSEQDX™, ISEQ™, NEXTSEQ™, or other sequencer systems from Illumina (San Diego, CA). In SBS, extension of sequencing primers along the template sequencing-ready nucleic acid fragments is monitored to determine the sequence of nucleotides in the templates. The 3'-ends of the templates and any flow cell-bound primers 18 (not attached to the copies) may be blocked to prevent interference with the sequencing reaction, and in particular, to prevent undesirable priming. The underlying chemical process can be polymerization (e.g., catalyzed by a polymerase enzyme) or ligation (e.g., catalyzed by a ligase enzyme). In a particular polymerase-based SBS process, fluorescently labeled nucleotides are added to the sequencing primer in a template dependent fashion such that detection of the order and type of nucleotides added to the sequencing primer can be used to determine the sequence of the template. For example, to initiate a first SBS cycle, one or more labeled nucleotides, DNA polymerase, etc., may be delivered into/through the flow cell 10, etc., where sequencing primer extension causes a labeled nucleotide to be incorporated. This incorporation can be detected through an imaging event. During an imaging event, an illumination system (not shown) may provide an excitation light to the flow cell 10, 10', 10''.

In some examples, the fluorescently labeled nucleotides can further include a reversible termination property that terminates further primer extension once a nucleotide has been added to the template. For example, a nucleotide analog having a reversible terminator moiety can be added to the template such that subsequent extension cannot occur until a deblocking agent is delivered to remove the moiety. Thus, for examples that use reversible termination, a deblocking reagent can be delivered to the flow cell, etc. (after detection occurs).

Wash(es) may take place between the various fluid delivery steps. The SBS cycle can then be repeated n times to extend the template by n nucleotides, thereby detecting a sequence of length n.

While SBS has been described in detail, it is to be understood that the flow cells 10, 10', 10'' described herein may be utilized with other sequencing protocol, for genotyping, or in other chemical and/or biological applications.

Other Flow Cell Applications

While sequencing has been described in detail, it is to be understood that the flow cells 10, 10', 10'' described herein may be utilized in other applications where a positively charged surface is desirable. As one example, the positively charged polymeric hydrogel 14 may be suitable for extracting DNA from lysates introduced to the flow cell 10, 10', 10''. For example, cells may be introduced into the lane(s) 20 or chambers 38, 38', and then a lysis buffer may be introduced. The DNA released from the cells may be attracted to the positively charged surface. An external immobilizing agent (e.g., oil, air) may or may not be used to further assist in containing the extracted DNA.

As another example, the positively charged polymeric hydrogel 14 may be used to repel proteins under certain pH conditions, thereby preventing unwanted protein binding at the surface. In these examples, the positively charged polymeric hydrogel 14 may or may not have the amplification primers 18 attached thereto.

The flow cells 10, 10', 10'' described herein may be utilized in other applications where a reversibly charged surface is desirable. The reversibly charged surface may be positively charged when the cationic moiety 16 is attached and negatively charged when the cationic moiety 16 is cleaved therefrom. The positively charged surface may help to attract DNA, and the negatively charged surface can help with elution. Negatively charged surfaces may also be desirable for pulling positively charged cells (e.g., bacteria) to the flow cell surface.

To further illustrate the present disclosure, an example is given herein. It is to be understood that this example is provided for illustrative purposes and is not to be construed as limiting the scope of the present disclosure.

NON-LIMITING WORKING EXAMPLE

A glass substrate with two lanes was utilized to prepare an example flow cell lane and a comparative example flow cell lane. Both lanes were silanized, and PAZAM was deposited thereon. Then, P5 and P7 primers were grafted to the PAZAM in the lanes. A lid was bonded using a UV curable adhesive to the substrate to fluidly isolate the two lanes.

Tris(hydropropyl)-phosphine (100 mM THP in 50 mM Tris-HCl buffer (pH 9)) was introduced to the example lane at 60° C. for about 2 minutes. The other (comparative) lane was not treated with the mixture.

The complexes used in this example included a solid support and sequencing-ready nucleic acid fragments attached to the solid support through an avidin-biotin linker. The library fragments of the complex were similar to those shown in FIG. 8B. The PCR free libraries were prepared in a tube following the TRUSEQ™ platform (Illumina, Inc.) protocol. The libraries were bound to the bead via hybridization to P7 primers, which were attached to the bead via biotin. The libraries were stained with Sytox green.

The complexes were introduced to the example and comparative example flow cell lanes by flowing a hybridization buffer containing the complexes (200 µL in the hybridization buffer) through each of the lanes. Seeding was initiated by releasing the library fragments from the complex. Library release was initiated by heating the flow cell above the melting temperature of the P7 primer. The fragments were hybridized and first strand extension was performed. The solid support and non-hybridized fragments were removed with a 0.2 M NaOH solution. Clustering was then performed using bridge amplification.

Figure 9B:
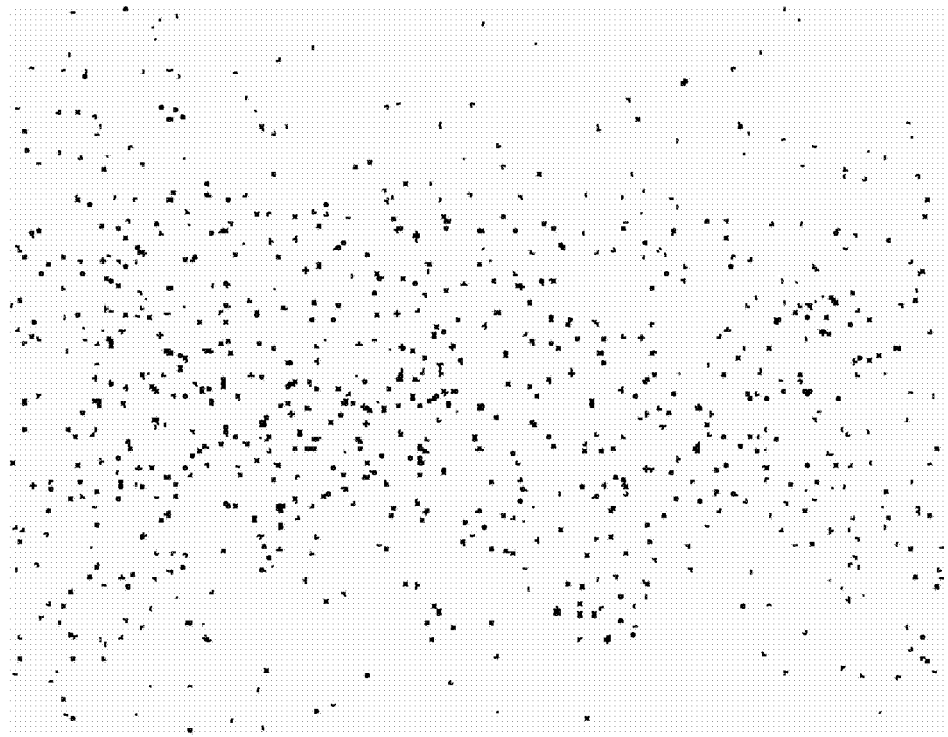
FIG. 9B is a schematic illustration of the interaction of the released DNA library fragments and the untreated hydrogel of the comparative flow cell of FIG. 9A.
Figure 9B:
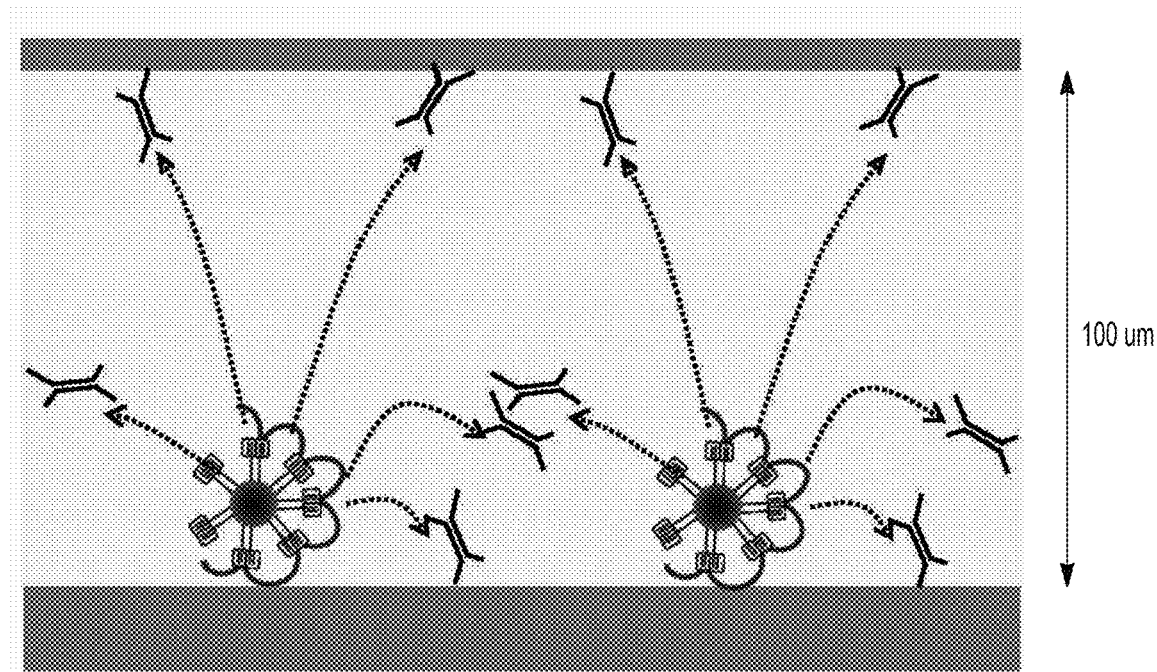

Micrographs of the example and comparative example lanes after clustering were taken, and the original coloring was inverted for clarity. As shown in FIG. 9A, the comparative lane, which was not treated with tris(hydropropyl)-phosphine, had relatively uniform library seeding across the surface. This is evidenced by the spread out darker spots in the inverted micrograph. FIG. 9B is a schematic illustration of the library release from the complexes on the comparative flow cell lane. The illustration depicts the width of the lane, and the scale bar represents the real dimension of the field of view for the 2D flow cell interior surface. As shown in the illustration of FIG. 9B, the library fragment transport and seeding is not restricted.

Figure 10A:
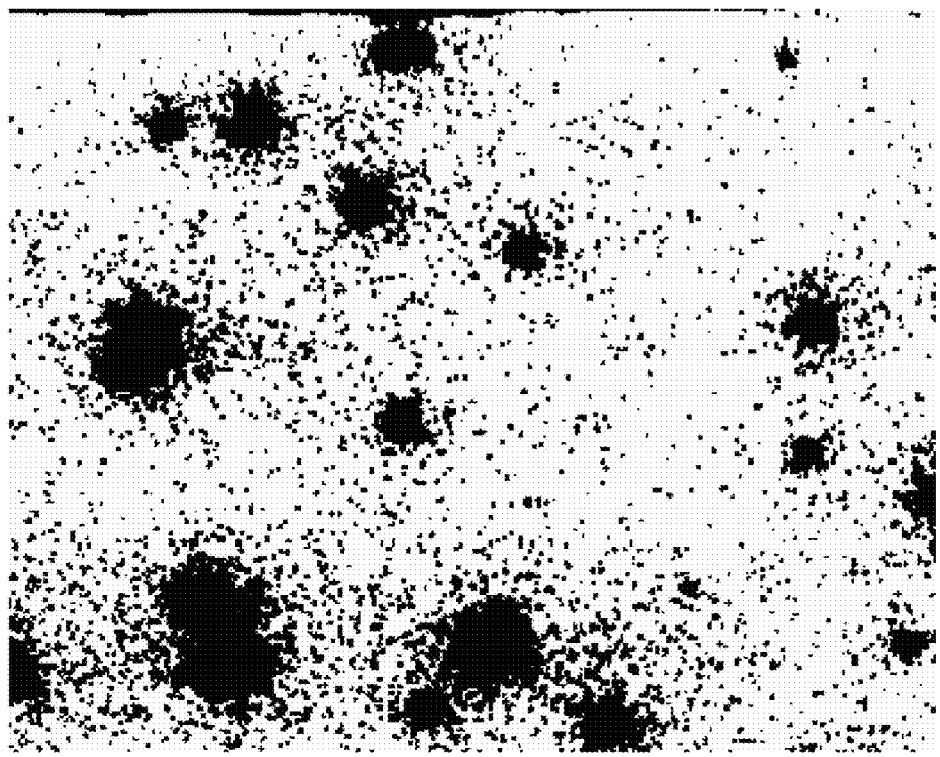
FIG. 10A is an inverted micrograph image (where the original dark portions of the image have been inverted to white and the original light portions of the image have been inverted to black) of released DNA library fragments on an example flow cell including a hydrogel treated with Tris (hydroxypropyl)-phosphine in a single-lane of a glass substrate.
Figure 10B:
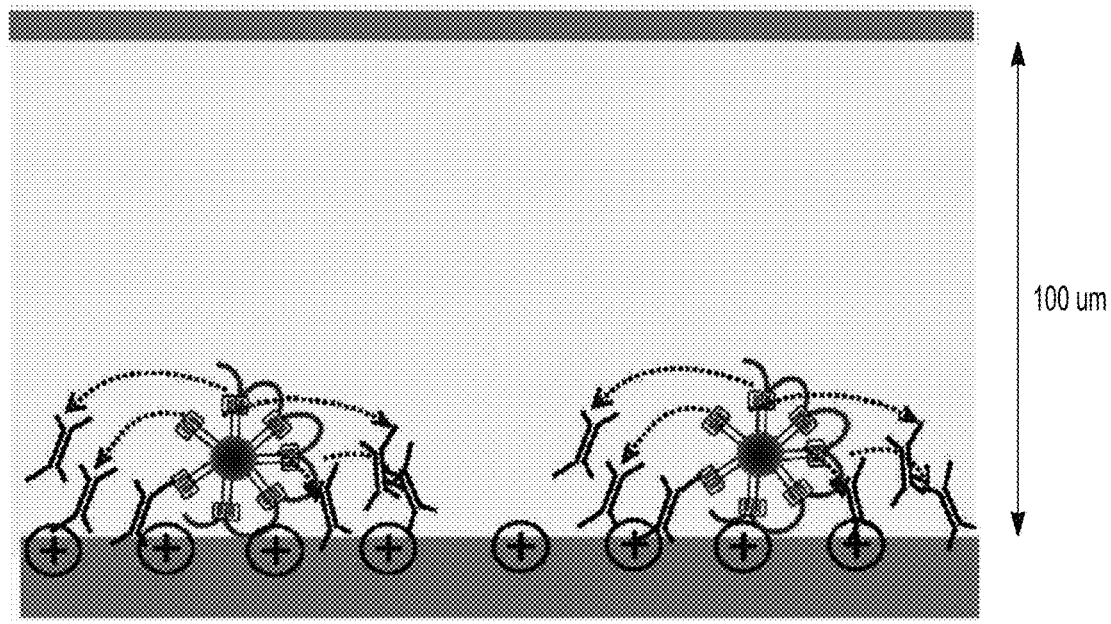
FIG. 10B is a schematic illustration of the interaction of the released DNA library fragments and the treated hydrogel of the example flow cell of FIG. 10A.

In contrast, as shown in FIG. 10A, the example lane (which was treated with tris(hydropropyl)-phosphine) had concentrated areas of DNA libraries. This is evidenced by the concentrated darker spots in the inverted micrograph. FIG. 10B is a schematic illustration of the library release from the complexes on the example flow cell lane. The illustration depicts the width of the lane, and the scale bar represents the real dimension of the field of view for the 2D flow cell interior surface. As shown in FIG. 10B, the library fragment transport and seeding is restricted because the negatively charged library fragments are attracted to the positively charged flow cell surface. These results illustrate that the tris(hydropropyl)-phosphine treated surface was positively charged, and thus was able to attract the DNA library fragments upon their release from the complexes.

Additional Notes

Furthermore, it is to be understood that the ranges provided herein include the stated range and any value or sub-range within the stated range, as if they were explicitly recited. For example, a range represented by from about 2 mm to about 300 mm, should be interpreted to include not only the explicitly recited limits of from about 2 mm to about 300 mm, but also to include individual values, such as about 15 mm, 22.5 mm, 245 mm, etc., and sub-ranges, such as from about 20 mm to about 225 mm, etc.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

While several examples have been described in detail, it is to be understood that the disclosed examples may be modified. Therefore, the foregoing description is to be considered non-limiting.

What is claimed is:

1. A flow cell, comprising:
   a substrate;
   a flow lane defined in the substrate;
   a cationic polymeric hydrogel on the substrate in at least a portion of the flow lane, the cationic polymeric hydrogel including a cationic moiety i) integrated into a monomeric unit of an initial polymeric hydrogel or ii) attached to the monomeric unit of the initial polymeric hydrogel through a linker;
   an amplification primer attached to the cationic polymeric hydrogel;
   a lid or second substrate bonded to the substrate;
   an input port in fluid communication with the flow lane; and
   an exit port in fluid communication with the flow lane.

2. The flow cell as defined in claim 1, wherein:
   the monomeric unit is N-(5-bromoacetamidylpentyl) acrylamide;
   the cationic moiety is a phosphonium cation; and
   the phosphonium cation displaces a bromine of the N-(5-bromoacetamidylpentyl) acrylamide.

3. The flow cell as defined in claim 2, wherein the phosphonium cation is selected from the group consisting of a tris(hydroxymethyl)phosphonium cation, a tris(hydroxypropyl)phosphonium cation, a tetrakis(hydroxymethyl) phosphonium cation, and a tris(2-carboxyethyl)phosphonium cation.

4. The flow cell as defined in claim 1, wherein:
   i) the monomeric unit includes a terminal azide group and the linker includes an alkyne group; or
   ii) the monomeric unit includes a terminal alkyne group and the linker includes an azide group.

5. The flow cell as defined in claim 4, wherein the cationic moiety includes a protonated amine group, a sulfonium ion, a quaternary ammonium cation, or combinations thereof.

6. The flow cell as defined in claim 4, wherein:
   the monomeric unit is N-(5-azidoacetamidylpentyl) acrylamide; and
   the cationic moiety is an N,N, N-trimethylethanolammonium cation.

7. The flow cell as defined in claim 4, wherein the linker further includes a cleavable disulfide bond, a photocleavable bond, a cleavable phosphodiester bond, or combinations thereof.

8. The flow cell as defined in claim 1, wherein:
   the monomeric unit is N-(5-azidoacetamidylpentyl) acrylamide;
   the linker includes a terminal alkyne group and a terminal bromine; and
   the cationic moiety is a phosphonium cation that displaces the terminal bromine.

9. The flow cell as defined in claim 1, wherein the substrate includes a plurality of depressions patterned therein within the flow lane and separated from each other by interstitial regions, and wherein the cationic polymeric hydrogel is positioned within each of the depressions.

10. A method, comprising:
    introducing a fluid, including a positively chargeable moiety, to a flow cell including:
    a substrate;
    a flow lane defined in the substrate;

an initial polymeric hydrogel on the substrate in at least a portion of the flow lane, the initial polymeric hydrogel having a surface moiety selected from the group consisting of a negatively chargeable atom, an azide group, and an alkyne group;
an amplification primer attached to the initial polymeric hydrogel;
a lid or second substrate bonded to the substrate;
an input port in fluid communication with the flow lane; and
an exit port in fluid communication with the flow lane; and
incubating the initial polymeric hydrogel in the fluid at a temperature and for a time, thereby forming a cationic polymeric hydrogel on the substrate in the at least the portion of the flow lane, the cationic polymeric hydrogel including a cationic moiety.

11. The method as defined in claim 10, wherein the positively chargeable moiety displaces the negatively chargeable atom of the initial polymeric hydrogel.

12. The method as defined in claim 11, wherein:
the surface moiety is the negatively chargeable atom;
the negatively chargeable atom is bromine; and
the positively chargeable moiety is selected from the group consisting of tris(hydroxymethyl)phosphine, tris(hydroxypropyl)phosphine, tetrakis(hydroxymethyl)phosphine, and tris(2-carboxyethyl)phosphine.

13. The method as defined in claim 11, wherein the fluid further includes a buffer having a pH ranging from 6 to 12.

14. The method as defined in claim 11, wherein the temperature ranges from about 18° C. to about 65° C. and the time ranges from about 1.5 minutes to about 5 minutes.

15. The method as defined in claim 10, wherein:
the surface moiety is the azide group or the alkyne group; and
the positively chargeable moiety covalently attaches to the surface moiety through a linker.

16. The method as defined in claim 15, wherein:
the surface moiety is the azide group;
the linker is an alkyne group; and
the cationic moiety includes a protonated amine group, a sulfonium ion, a quaternary ammonium cation, or combinations thereof.

17. The method as defined in claim 15, wherein:
the surface moiety is the alkyne group;
the linker is an azide group; and
the cationic moiety includes a protonated amine group, a sulfonium ion, a quaternary ammonium cation, or combinations thereof.

18. The method as defined in claim 15, wherein a compound includes the positively chargeable moiety attached to the linker, and wherein the compound is propargyl choline bromide.

19. The method as defined in claim 15, wherein the fluid includes a water.

20. The method as defined in claim 15, wherein the temperature ranges from about 18° C. to about 60° C. and the time ranges from about 30 minutes to about 12 hours.

21. The method as defined in claim 15, further comprising adding a catalyst, a ligand, and a reducing agent to the flow cell with the fluid.

* * * * *